US012626805B2

(12) United States Patent
Carson et al.

(10) Patent No.: US 12,626,805 B2
(45) Date of Patent: May 12, 2026

(54) SYSTEM, METHOD, AND APPARATUS FOR PET CONDITION DETECTION

(71) Applicant: Tractive Inc., Seattle, WA (US)

(72) Inventors: Aletha Carson, Portland, OR (US); Robert Donald Chambers, Seattle, WA (US); Nathanael Christian Yoder, San Francisco, CA (US)

(73) Assignee: Tractive Inc., Seattle, WA (US)

( * ) Notice: Subject to any disclaimer, the term of this patent is extended or adjusted under 35 U.S.C. 154(b) by 0 days.

(21) Appl. No.: 18/556,301

(22) PCT Filed: Apr. 19, 2022

(86) PCT No.: PCT/US2022/025368
§ 371 (c)(1),
(2) Date: Oct. 19, 2023

(87) PCT Pub. No.: WO2022/225945
PCT Pub. Date: Oct. 27, 2022

(65) Prior Publication Data
US 2024/0185988 A1 Jun. 6, 2024

Related U.S. Application Data

(60) Provisional application No. 63/176,812, filed on Apr. 19, 2021.

(51) Int. Cl.
*G16H 20/70* (2018.01)
*A01K 11/00* (2006.01)
(Continued)

(52) U.S. Cl.
CPC ........... *G16H 20/70* (2018.01); *A01K 11/008* (2013.01); *A01K 29/005* (2013.01); *A61D 99/00* (2013.01); *G16H 10/20* (2018.01); *G16H 40/67* (2018.01)

(58) Field of Classification Search
None
See application file for complete search history.

(56) References Cited

U.S. PATENT DOCUMENTS 9,615,547 B2 * 4/2017 Menkes .............. A61B 5/0022
10,551,935 B2 2/2020 Valafar et al.
(Continued)

FOREIGN PATENT DOCUMENTS

JP 2019516454 A 6/2019
WO 2016140332 A1 9/2016
(Continued)

OTHER PUBLICATIONS

Griffies et al., "Wearable sensor shown to specifically quantify pruritic behaviors in dogs", Apr. 3, 2018, BMC Veterinary Research 14, 124 (Year: 2018).*
(Continued)

*Primary Examiner* — Anne-Marie K Alderson
(74) *Attorney, Agent, or Firm* — Bookoff McAndrews, PLLC

(57) ABSTRACT

In one embodiment, a method includes accessing sensor data captured by sensors, wherein the sensor data is associated with a first pet, detecting activities of the first pet within a specified time period based on the sensor data, determining health indicators of the first pet based on one or more of the activities, wherein the health indicators are based on metrics associated with the one or more activities, generating a wellness assessment of the first pet based on the health indicators, wherein the wellness assessment comprises one or more of a wellness score or an alert of a possible medical condition, and sending instructions to a user device for presenting the wellness assessment of the first pet to a user.

20 Claims, 24 Drawing Sheets

(51) Int. Cl.

| | |
|---|---|
| *A01K 29/00* | (2006.01) |
| *A61D 99/00* | (2006.01) |
| *G16H 10/20* | (2018.01) |
| *G16H 40/67* | (2018.01) |

(56) References Cited

U.S. PATENT DOCUMENTS

| | | | | |
|---|---|---|---|---|
| 10,687,516 | B1* | 6/2020 | Van Eeden | A01K 11/006 |
| 2011/0184781 | A1* | 7/2011 | Hussam | G16H 40/20 |
| | | | | 705/7.32 |
| 2013/0308839 | A1* | 11/2013 | Taylor | G16H 30/20 |
| | | | | 382/128 |
| 2014/0275824 | A1* | 9/2014 | Couse | G16H 40/60 |
| | | | | 600/301 |
| 2015/0112709 | A1* | 4/2015 | Bowman | G16H 50/70 |
| | | | | 705/2 |
| 2015/0181840 | A1* | 7/2015 | Tupin, Jr. | A61B 5/0008 |
| | | | | 600/483 |
| 2016/0042038 | A1 | 2/2016 | Schumacher et al. | |
| 2016/0302393 | A1* | 10/2016 | Pradeep | A01K 29/005 |
| 2017/0147775 | A1* | 5/2017 | Ohnemus | G16H 50/50 |
| 2017/0272843 | A1* | 9/2017 | Dror | A01K 29/005 |
| 2018/0253991 | A1* | 9/2018 | Tang | G16H 50/30 |
| 2018/0263220 | A1* | 9/2018 | Schab | G06N 5/048 |
| 2018/0292910 | A1* | 10/2018 | Valafar | G06F 3/017 |
| 2019/0110684 | A1* | 4/2019 | Coen | G16H 40/67 |
| 2019/0133488 | A1* | 5/2019 | Meftah | A61B 5/349 |
| 2019/0167106 | A1* | 6/2019 | Couse | A61B 5/6802 |
| 2019/0224434 | A1* | 7/2019 | Silver | A61N 1/3904 |
| 2020/0058404 | A1* | 2/2020 | Nazem | G16H 20/60 |
| 2020/0060545 | A1* | 2/2020 | Maher | A61B 5/01 |
| 2020/0381119 | A1* | 12/2020 | Gibbs | G16H 40/67 |
| 2021/0065277 | A1* | 3/2021 | Bramson | G06Q 30/0631 |
| 2021/0089945 | A1* | 3/2021 | Gibbs | G06N 5/02 |
| 2021/0090712 | A1* | 3/2021 | Donavon | G09B 19/00 |
| 2021/0134459 | A1* | 5/2021 | Crawford | G16H 50/30 |
| 2022/0159934 | A1* | 5/2022 | Molloy | A01K 29/005 |
| 2022/0199235 | A1* | 6/2022 | Knickerbocker | G16H 40/67 |
| 2022/0367059 | A1 | 11/2022 | Mott et al. | |

FOREIGN PATENT DOCUMENTS

| | | | | |
|---|---|---|---|---|
| WO | 2016185742 A1 | 11/2016 | | |
| WO | WO-2017061860 A1 * | 4/2017 | | A61B 5/4023 |
| WO | 2017191036 A1 | 11/2017 | | |
| WO | WO 2020/264360 A1 | 12/2020 | | |

OTHER PUBLICATIONS

Wernimont et al., Use of Accelerometer Activity Monitors to Detect Changes in Pruritic Behaviors: Interim Clinical Data on 6 Dogs, Sensors 2018, 18(1), 249; https://doi.org/10.3390/s18010249, Jan. 2018 (Year: 2018).*

International Search Report and Written Opinion mailed Aug. 9, 2022 for International Application No. PCT/US2022/025368.

* cited by examiner

850

Activity

Step 1: Daily & Baseline Values

Step 2: Score Each Component

COMPONENT SCORES

Step 3: Combine to One "Activity" Score

ACTIVITY DIMENSION SCORE

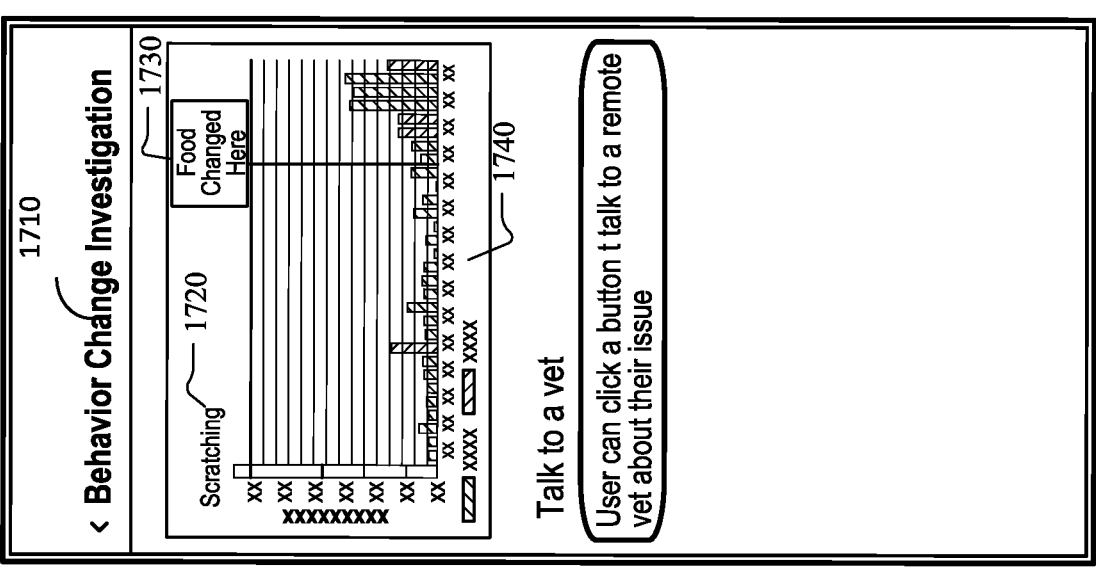
FIG. 17
FIG. 16
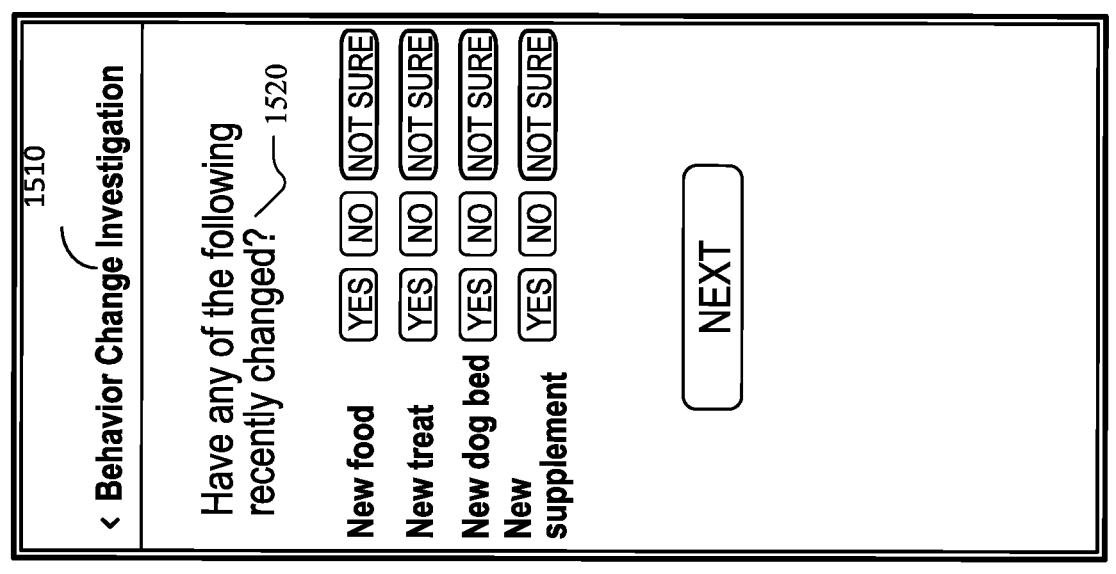
FIG. 15

2100

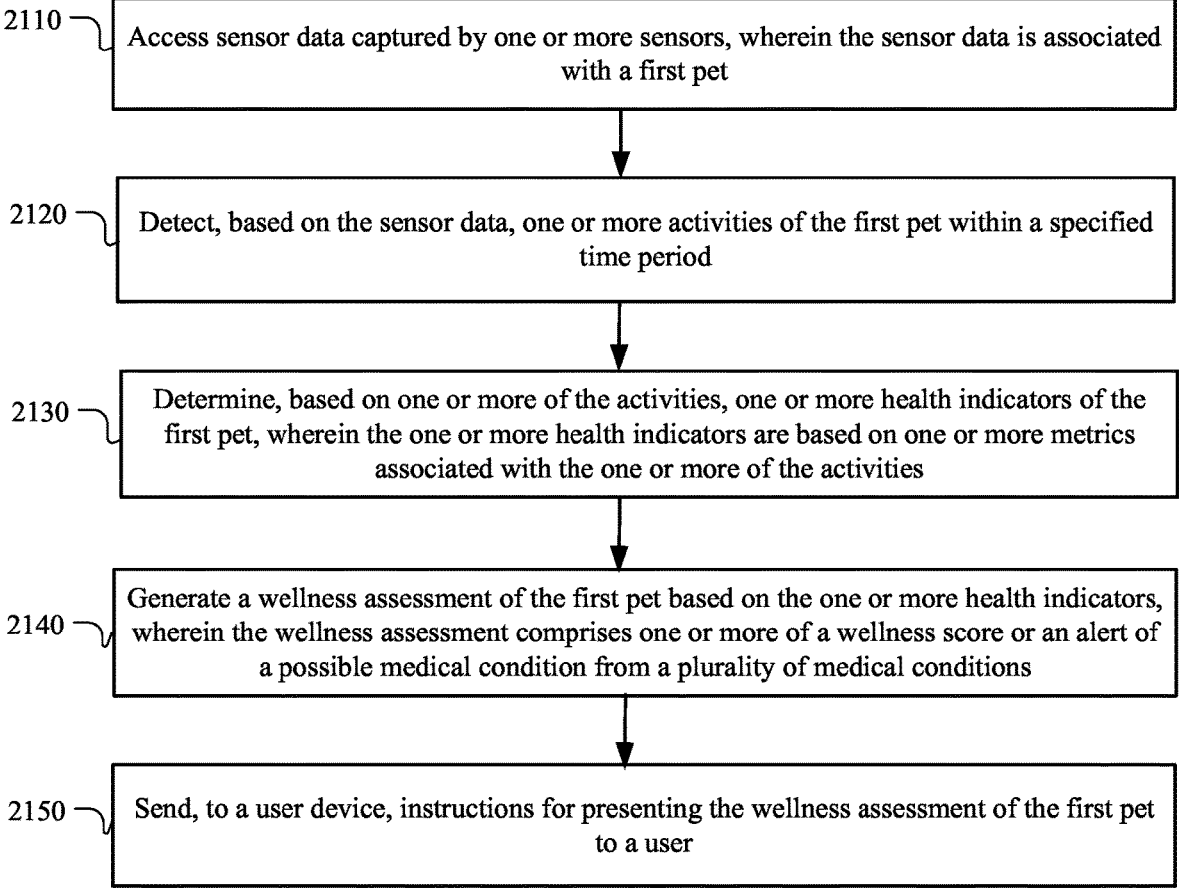

2110 — Access sensor data captured by one or more sensors, wherein the sensor data is associated with a first pet 2120 — Detect, based on the sensor data, one or more activities of the first pet within a specified time period 2130 — Determine, based on one or more of the activities, one or more health indicators of the first pet, wherein the one or more health indicators are based on one or more metrics associated with the one or more of the activities 2140 — Generate a wellness assessment of the first pet based on the one or more health indicators, wherein the wellness assessment comprises one or more of a wellness score or an alert of a possible medical condition from a plurality of medical conditions 2150 — Send, to a user device, instructions for presenting the wellness assessment of the first pet to a user

*FIG. 21*

SYSTEM, METHOD, AND APPARATUS FOR PET CONDITION DETECTION

CROSS-REFERENCE TO RELATED APPLICATIONS

This application is a U.S. National Stage Patent Application under 35 U.S.C. § 371 of International Patent Application No. PCT/US2022/025368, filed Apr. 19, 2022, which claims the benefit, under 35 U.S.C. § 119(e), of U.S. Provisional Patent Application No. 63/176,812, filed 19 Apr. 2021, both of which are incorporated herein by reference.

TECHNICAL FIELD

The embodiments described in the disclosure relate to monitoring of pet activity. For example, some non-limiting embodiments relate to monitoring of pet activity to help detect a health condition of a pet.

BACKGROUND

Mobile devices and/or wearable devices have been fitted with various hardware and software components that can help track or monitor human activity. The data resulting from the monitored activity can be collected, analyzed, and displayed. For example, a mobile device and/or wearable devices can be used to track the number of steps or the heart rate of a human during a given period of time. The number of steps or heart rate can then be displayed on a user graphic interface of the mobile device or wearable device. Beyond human monitoring, the ever-growing emphasis on pet safety and health has resulted in an increased need to monitor pet behavior. Accordingly, there is an ongoing demand in the pet product industry for a system and/or method for monitoring pet activity.

SUMMARY OF PARTICULAR EMBODIMENTS

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages, and in accordance with the purpose of the disclosed subject matter, as embodied and broadly described, the disclosed subject matter presents systems, methods, and apparatuses that can be used to collect, receive and/or analyze data. For example, certain non-limiting embodiments can be used to monitor and track pet activity.

In certain non-limiting embodiments, the disclosure describes a method for monitoring pet activity and determining pet wellness accordingly. The method includes determining one or more health indicators of a pet based on collected, received and/or analyzed data. The method also includes performing a wellness assessment of the pet based on the one or more health indicators of the pet. In addition, the method includes displaying one or more notifications to a pet owner based on the wellness assessment of the pet at a mobile device.

In certain non-limiting embodiments, one or more computing systems can access sensor data captured by one or more sensors. The sensor data can be associated with a first pet. The computing systems can then detect, based on the sensor data, one or more activities of the first pet within a specified time period. The computing systems can then determine, based on one or more of the activities, one or more health indicators of the first pet. In certain non-limiting embodiments, the one or more health indicators can be based on one or more metrics associated with the one or more of the activities. The computing systems can further generate a wellness assessment of the first pet based on the one or more health indicators. The wellness assessment can comprise one or more of a wellness score or an alert of a possible medical condition from a plurality of medical conditions. In certain non-limiting embodiments, the computing systems can then send, to a user device, instructions for presenting the wellness assessment of the first pet to a user.

In certain non-limiting embodiments, one or more computer-readable non-transitory storage media embodying software is operable when executed to access sensor data captured by one or more sensors. The sensor data can be associated with a first pet. The computer-readable non-transitory storage media embodying software is further operable when executed to detect, based on the sensor data, one or more activities of the first pet within a specified time period. The computer-readable non-transitory storage media embodying software is further operable when executed to determine, based on one or more of the activities, one or more health indicators of the first pet. In some embodiments, the one or more health indicators can be based on one or more metrics associated with the one or more of the activities. The computer-readable non-transitory storage media embodying software is further operable when executed to generate a wellness assessment of the first pet based on the one or more health indicators. In some embodiments, the wellness assessment can comprise one or more of a wellness score or an alert of a possible medical condition from a plurality of medical conditions. The computer-readable non-transitory storage media embodying software is further operable when executed to send, to a user device, instructions for presenting the wellness assessment of the first pet to a user.

In certain non-limiting embodiments, a system can comprise one or more processors and a non-transitory memory coupled to the processors comprising instructions executable by the processors. The processors are operable when executing the instructions to access sensor data captured by one or more sensors. In some embodiments, the sensor data can be associated with a first pet. The processors are further operable when executing the instructions to detect, based on the sensor data, one or more activities of the first pet within a specified time period. The processors are further operable when executing the instructions to determine, based on one or more of the activities, one or more health indicators of the first pet. In some embodiments, the one or more health indicators can be based on one or more metrics associated with the one or more of the activities. The processors are further operable when executing the instructions to generate a wellness assessment of the first pet based on the one or more health indicators. In some embodiments, the wellness assessment can comprise one or more of a wellness score or an alert of a possible medical condition from a plurality of medical conditions. The processors are further operable when executing the instructions to send, to a user device, instructions for presenting the wellness assessment of the first pet to a user.

Furthermore, the disclosed embodiments of the methods, computer readable non-transitory storage media, and systems can have further non-limiting features as described below.

In certain non-limiting embodiments, the one or more sensors can comprise one or more of an actuator, a gyroscope, a magnetometer, a microphone, or a pressure sensor. The one or more sensors can be associated with a wearable device worn by or attached to the first pet. In some embodiments, the computing systems can detect an unwanted rotation of the wearable device. The computing systems can then apply one or more data transformations to the sensor data to correct the unwanted rotation. In alternative embodiments, the computing systems can determine an orientation of the wearable device. The computing systems can further process the sensor data based on the orientation of the wearable device.

In certain non-limiting embodiments, generating the wellness assessment of the first pet can be further based on one or more of health status data of the first pet, demographic information of the first pet, genetic data of the first pet, location of the first pet, weather information of the location of the first pet, or environment data of the location of the first pet. In some embodiments, the wellness assessment can comprise one or more wellness scores. The computing systems can calculate the one or more wellness scores based on one or more of an amount of time of the first pet performing an activity, an intensity point of the first pet performing the activity, a percentage of the amount of time of the first pet performing the activity compared to a goal time determined based on data associated with a plurality of second pets, or a percentage of the intensity point of the first pet performing the activity compared to a goal intensity point determined based on the data associated with the plurality of second pets. In alternative embodiments, the computing systems can rescale one or more of the metrics into a predetermined range. The computing systems can then generate the one or more wellness scores based on the rescaled metrics.

In certain non-limiting embodiments, the computing systems can compare at least one of the determined health indicators to one stored corresponding health indicator. The computing systems can further detect a threshold difference between the at least one determined health indicator and the stored corresponding health indicator. Accordingly, the wellness assessment can further comprise the detected threshold difference between the at least one determined health indicator and the stored corresponding health indicator. In some embodiments, the one or more health indicators can be associated with one or more weights, respectively. The computing systems can then generate the one or more wellness scores based on the one or more weights.

In certain non-limiting embodiments, the one or more activities can comprise one or more of a posture comprising one or more of lying down, sitting, standing, walking, or vigorous, or a behavior comprising one or more of drinking, eating, licking an object, self-licking, petting, rubbing, scratching, shaking, or sniffing. The plurality of medical conditions can comprise one or more of a dermatological condition, an ear infection, arthritis, a cardiac episode, a gastrointestinal condition, malaise, a tooth fracture, a cruciate ligament tear, or a pancreatic episode.

In certain non-limiting embodiments, the computing systems can determine effectiveness of a pet product based on the one or more health indicators, wherein the pet product comprises one or more of a medication, a pharmaceutical drug, a pet food, or a prescribed treatment by a veterinarian.

The computing systems can further transmit the determined effectiveness of the pet product to a veterinarian or a manufacturer of the pet product.

In certain non-limiting embodiments, the computing systems can determine a health recommendation for the first pet based on the wellness assessment. The health recommendation can comprise one or more of a recommendation for a pet product or a recommendation for a veterinarian visit.

In certain non-limiting embodiments, detecting the one or more activities of the first pet or determining the one or more health indicators of the first pet can be based on one or more machine learning models. The one or more machine learning models can be trained based on a plurality of data associated with a plurality of second pets. In some embodiments, the computing systems can send, to the user device, instructions for presenting a survey or questionnaire corresponding to the wellness assessment of the first pet. The computing systems can then receive, from the user device, feedback from the user in response to the survey or questionnaire. The computing systems can further update the one or more machine learning models based on the feedback from the user.

In certain non-limiting embodiments, the wellness assessment can comprise one or more alerts of a possible medical condition. Correspondingly, the computing systems can customize a sensitivity or a specificity of the one or more alerts for the user. In some embodiments, the computing systems can generate a causal explanation for the possible medical condition. The computing systems can further send, to the user device, instructions for presenting the causal explanation. In alternative embodiments, the computing systems can generate an estimated timeline for the possible medical condition. The computing systems can further send, to the user device, instructions for presenting the estimated timeline.

It is to be understood that both the foregoing general description and the following detailed description are exemplary and are intended to provide further explanation of the disclosed subject matter claimed.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure:

FIGS. 15 and 16 illustrate an example of a user interface according to certain non-limiting embodiments.

FIG. 17 illustrates an example of a user interface according to certain non-limiting embodiments.

FIG. 21 illustrates an example method for pet wellness assessment.

DESCRIPTION OF EXAMPLE EMBODIMENTS

Figure 1:
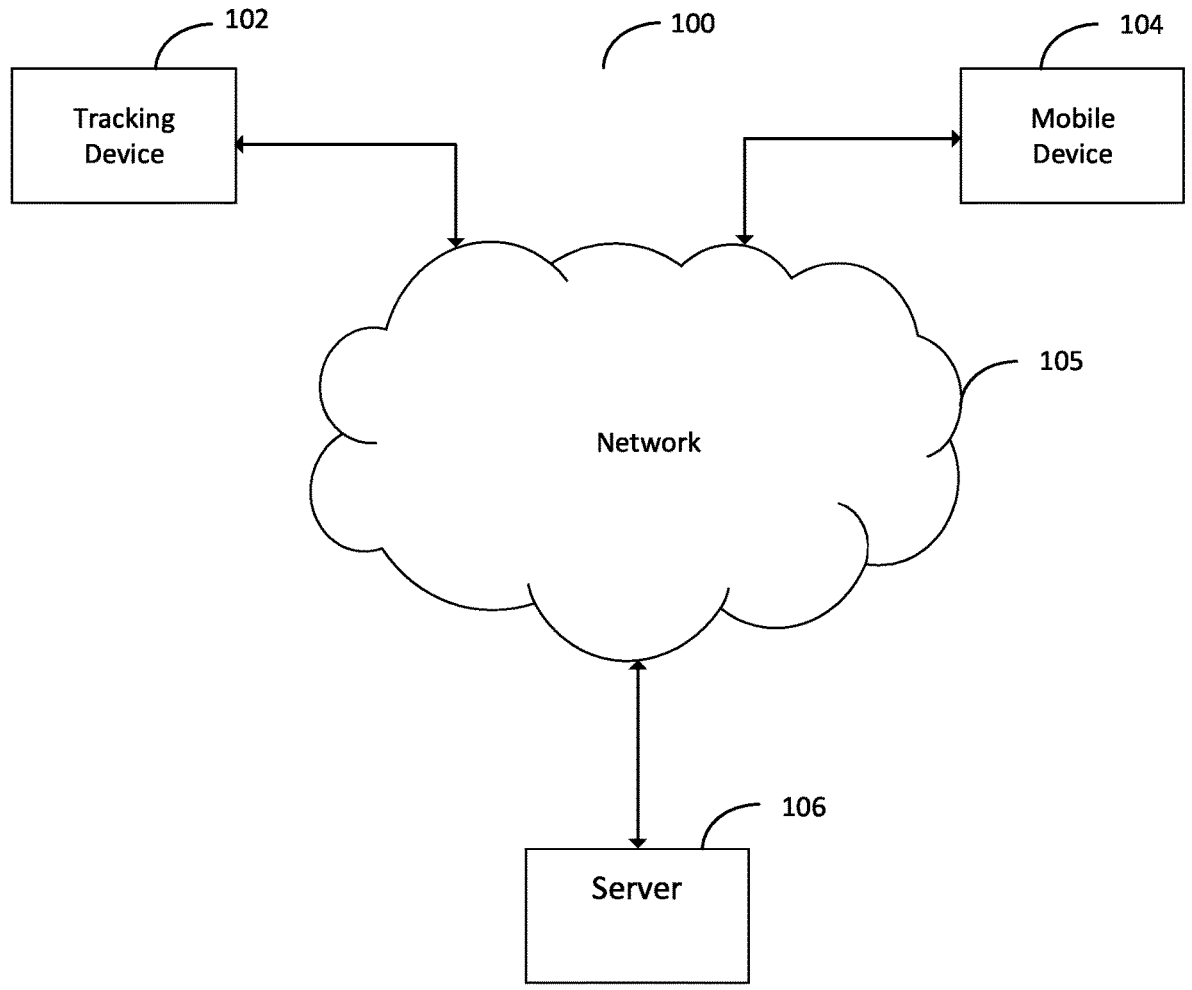
FIG. 1 illustrates a system used for pet monitoring according to certain non-limiting embodiments.

The present disclosure will now be described more fully hereinafter with reference to the accompanying drawings, which form a part hereof, and which show, by way of illustration, certain example embodiments. Subject matter can, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter can be embodied as methods, devices, components, and/or systems. Accordingly, embodiments can, for example, take the form of hardware, software, firmware or any combination thereof (other than software per se). The following detailed description is, therefore, not intended to be taken in a limiting sense.

The present disclosure provides systems, methods, and/or devices that can monitor, analyze and/or track pet activity. The presently disclosed subject matter addresses needs associated with assessing and/or monitoring the health and wellness of pets. Specifically, data related to the tracked or monitored activity of a pet can be collected and used to detect and/or evaluate one or more potential and/or actual health risks (collectively "health risk" or "health risks") related to a pet. The identified health risks, as well as a summary of any or all collected data, can then be transmitted to and/or displayed for or by a pet owner, a pet caretaker, a researcher, a veterinarian, a veterinary technician and/or another party.

PCT Application No. PCT/US20/39909 is hereby incorporated by reference. The entire subject matter disclosed in the above referenced applications, including the specification, claims, and figures are incorporated herein.

In the detailed description herein, references to "embodiment," "an embodiment," "one non-limiting embodiment," "in various embodiments," etc., indicate that the embodiment(s) described can include a particular feature, structure, or characteristic, but every embodiment might not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

In general, terminology can be understood at least in part from usage in context. For example, terms, such as "and", "or", or "and/or," as used herein can include a variety of meanings that can depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, can be used to describe any feature, structure, or characteristic in a singular sense or can be used to describe combinations of features, structures or characteristics in a plural sense. Similarly, terms, such as "a," "an," or "the," again, can be understood to convey a singular usage or to convey a plural usage, depending at least in part upon context. In addition, the term "based on" can be understood as not necessarily intended to convey an exclusive set of factors and can, instead, allow for existence of additional factors not necessarily expressly described, again, depending at least in part on context.

As used herein, the terms "comprises," "comprising," or any other variation thereof, are intended to cover a non-exclusive inclusion, such that a process, method, article, or apparatus that comprises a list of elements does not include only those elements but can include other elements not expressly listed or inherent to such process, method, article, or apparatus.

The terms "animal" or "pet" as used in accordance with the present disclosure can refer to domestic animals including, domestic dogs, domestic cats, horses, cows, ferrets, rabbits, pigs, rats, mice, gerbils, hamsters, goats, and the like. Domestic dogs and cats are particular non-limiting examples of pets. The term "animal" or "pet" as used in accordance with the present disclosure can also refer to wild animals, including, but not limited to bison, elk, deer, venison, duck, fowl, fish, and the like.

The term "pet product" can include, for example, without limitation, any type of product, service, or equipment that is designed, manufactured, and/or intended for use by a pet. For example, the pet product can be a toy, a chewable, a food, an item of clothing, a collar, a medication, a pharmaceutical drug, a health tracking device, a location tracking device, and/or any combination thereof. In another example a pet product can include a genetic or DNA testing service for pets.

The term "pet owner" can include any person, organization, and/or collection of persons that owns and/or is responsible for any aspect of the care of a pet. For example, a "pet owner" can include a pet caretaker, pet caregiver, a researcher, a veterinarian, a veterinary technician, and/or another party.

As used herein, a "training data set" can include one or more images or videos and associated data to train a machine learning model. Each training data set can comprise a training image of one or more products, data, and a corresponding output associated with the image. A training data set can include one or more images or videos of fecal matter. A training data set can be collected via one or more client devices (e.g., crowd-sourced) or collected from other sources (e.g., a database). In certain non-limiting embodiments, the training data set for a wellness assessment of a pet can include data from both a treatment group and a control group.

Certain non-limiting embodiments are described below with reference to block diagrams and operational illustrations of methods, processes, devices, and apparatus. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of: a general purpose computer to alter its function to a special purpose; a special purpose computer; ASIC; or other programmable digital data processing apparatus, such that the instructions, which execute via the processor of the computer or other programmable data processing apparatus, implement the functions/acts specified in the block diagrams or operational block or blocks, thereby transforming their functionality in accordance with embodiments herein.

In some non-limiting embodiments, a computer readable medium (or computer-readable storage medium/media) stores computer data, which data can include computer program code (or computer-executable instructions) that is executable by a computer, in machine readable form. By way of example, and not limitation, a computer readable medium can comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

In certain non-limiting embodiments, the term "server", such as server 106 shown in FIG. 1, should be understood to refer to a service point which provides processing, database, and communication facilities. By way of example, and not limitation, the term "server" can refer to a single, physical processor with associated communications and data storage and database facilities, or it can refer to a networked or clustered complex of processors, such as an elastic computer cluster, and associated network and storage devices, as well as operating software and one or more database systems and application software that support the services provided by the server. The server, for example, can be a cloud-based server, a cloud-computing platform, or a virtual machine. Servers can vary widely in configuration or capabilities, but generally a server can include one or more central processing units and memory. A server can also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For some non-limiting embodiments, a "network", such as network 108 shown in FIG. 1, should be understood to refer to a network that can couple devices so that communications can be exchanged, such as between a server and a client device or other types of devices, including between wireless devices coupled via a wireless network, for example. A network can also include mass storage, such as network attached storage (NAS), a storage area network (SAN), or other forms of computer or machine-readable media, for example. A network can include the Internet, one or more local area networks (LANs), one or more wide area networks (WANs), wire-line type connections, wireless type connections, cellular or any combination thereof. Likewise, sub-networks, which can employ differing architectures or can be compliant or compatible with differing protocols, can interoperate within a larger network. Various types of devices can, for example, be made available to provide an interoperable capability for differing architectures or protocols. As one illustrative example, a router can provide a link between otherwise separate and independent LANS.

A communication link or channel can include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as can be known to those skilled in the art. Furthermore, a computing device or other related electronic devices can be remotely coupled to a network, such as via a wired or wireless line or link, for example.

In certain non-limiting embodiments, a "wireless network" should be understood to couple client devices with a network. A wireless network can employ stand-alone ad-hoc networks, mesh networks, wireless land area network (WLAN), cellular networks, or the like. A wireless network can further include a system of terminals, gateways, routers, or the like coupled by wireless radio links, or the like, which can move freely, randomly or organize themselves arbitrarily, such that network topology can change, at times even rapidly.

A wireless network can further employ a plurality of network access technologies, including Wi-Fi, Long Term Evolution (LTE), WLAN, Wireless Router (WR) mesh, or 2nd, 3rd, 4th, 5th generation (2G, 3G, 4G, or 5G) cellular technology, or the like. Network access technologies can allow wide area coverage for devices, such as client devices with varying degrees of mobility, for example.

For example, a network can provide radio frequency (RF) or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP LTE, LTE Advanced, Wideband Code Division Multiple Access (WCDMA), Bluetooth, 802.11b/g/n, or the like. A wireless network can include virtually any type of wireless communication mechanism by which signals can be communicated between devices, such as a client device or a computing device, between or within a network, or the like.

A computing device can send or receive signals, such as via a wired or wireless network, or can process or store signals, such as in memory as physical memory states. For example, a computing device can operate as a server and can include, as examples, dedicated rack-mounted servers, desktop computers, laptop computers, set top boxes, integrated devices combining various features, such as two or more features of the foregoing devices, or the like. Servers can vary widely in configuration or capabilities, but generally a server can include one or more central processing units and memory. A server can also include one or more mass storage devices, one or more power supplies, one or more wired or wireless network interfaces, one or more input/output interfaces, or one or more operating systems.

In certain non-limiting embodiments, a wearable device or tracking device, such as tracking device 102 shown in FIG. 1, can include one or more sensors. The term "sensor" can refer to any hardware or software used to detect a variation of a physical quantity caused by activity or movement of the pet, such as an actuator, a gyroscope, a magnetometer, a microphone, pressure sensor, or any other device that can be used to detect an object's displacement. In one non-limiting example, the sensor can be a three-axis accelerometer. The one or more sensors or actuators can be included in a microelectromechanical system (MEMS). A MEMS, also referred to as a MEMS device, can include one or more miniaturized mechanical and/or electro-mechanical elements that function as sensors and/or actuators and can help to detect positional variations, movement, and/or acceleration. In other embodiments any other sensor or actuator can be used to detect any physical characteristic, variation, or quantity. The wearable device, also referred to as a collar device, can also include one or more transducers. The transducer can be used to transform the physical characteristic, variation, or quantity detected by the sensor and/or actuator into an electrical signal, which can be transmitted from the one or more wearable device through a network to a server.

FIG. 1 illustrates a system diagram used to track and/or monitor a pet according to certain non-limiting embodiments. In particular, as illustrated in FIG. 1, the system 100 can include a tracking device 102, a mobile device 104, a server 106, and/or a network 108. Tracking device 102 can be a wearable device worn or attached to a pet. For example, the wearable device can be placed on a collar of the pet, and can be used to track, monitor, and/or detect the activity of the pet using one or more sensors. In certain non-limiting embodiments, the one or more sensors can be used to sense various body movements of a pet, such as bodily movement associated with itching, scratching, licking, walking, drinking, eating, sleeping, and shaking, and/or any other bodily movement associated with an action performed by the pet. Itching, for example, can be a category of pet movement including scratching, biting, licking, chewing, nibbling, and/or rubbing. In certain examples, the one or more sensors can detect activity of a pet either before or after a medical procedure, administration of a medication or a pharmaceutical, or a veterinary visit, such as a castration or ovariohysterectomy visit.

As illustrated in FIG. 1, a tracking device 102 can include a computing device designed to be worn, or otherwise carried, by a user or other entity, such as a pet or animal.

Figure 2:
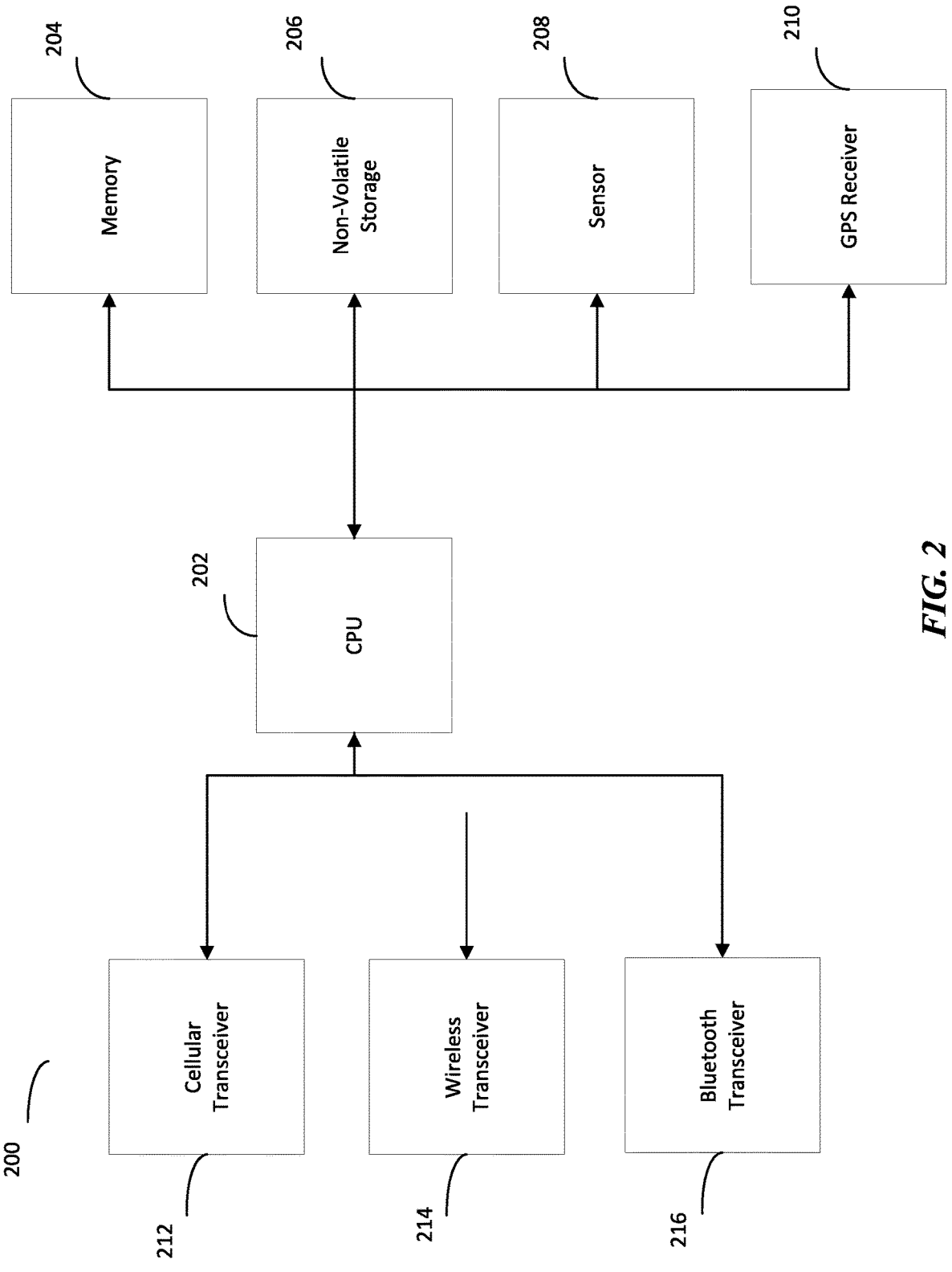
FIG. 2 illustrates a device used for pet monitoring according to certain non-limiting embodiments.

In certain non-limiting embodiments, tracking device 102 can include the hardware illustrated in FIG. 2. Tracking device 102, for example, can collect data generated by various hardware or software components, generally referred to as sensors, present within the tracking device 102. For example, a GPS receiver or one or more sensors, such as accelerometer, gyroscope, or any other device or component used to record, collect, or receive data regarding the movement or activity of the tracking device 102. The activity of tracking device 102, in some non-limiting embodiments, can mimic the movement of the pet on which the tracking device is located. While tracking device 102 can be attached to the collar of the pet, in other embodiments tracking device 102 can be attached to any other item worn by the pet. In some non-limiting embodiments, tracking device 102 can be located on or inside the pet itself, such as, for example, a microchip implanted within the pet.

As discussed in more detail herein, tracking device 102 can further include a processor for processing the one or more data collected from one or more sensors of tracking device 102. The processor can be embodied by any computational or data processing device, such as a central processing unit (CPU), digital signal processor (DSP), application specific integrated circuit (ASIC), programmable logic devices (PLDs), field programmable gate arrays (FPGAs), digitally enhanced circuits, or comparable device or a combination thereof. The processors can be implemented as a single controller, or a plurality of controllers or processors. In some non-limiting embodiments, the tracking device 102 can specifically be configured to collect, sense, or receive data, and/or pre-process data prior to transmittal. In addition to sensing, recording, and/or processing data, tracking device 102 can further be configured to transmit data, including location and any other data monitored or tracked, to other devices or severs via network 108. In certain non-limiting embodiments, tracking device 102 can transmit any data tracked or monitored data continuously to the network. In other non-limiting embodiments, tracking device 102 can discretely transmit any tracked or monitored data. Discrete transmittal can be transmitting data after a finite period of time. For example, tracking device 102 can transmit data once an hour. This can help to reduce the battery power consumed by tracking device 102, while also conserving network resources, such as bandwidth. More information on tracking devices can be found in U.S. patent application Ser. No. 29/696,311, filed 26 Jun. 2019, and U.S. patent application Ser. No. 29/696,315, filed 26 Jun. 2019, each of which is incorporated by reference.

As shown in FIG. 1, tracking device 102 can communicate with network 108. Although illustrated as a single network, network 108 can comprise multiple or a plurality of networks facilitating communication between devices. Network 108 can be a radio-based communication network that uses any available radio access technology. Available radio access technologies can include, for example, Bluetooth, wireless local area network ("WLAN"), Global System for Mobile Communications (GMS), Universal Mobile Telecommunications System (UMTS), any Third Generation Partnership Project ("3GPP") Technology, including Long Term Evolution ("LTE"), LTE-Advanced, Third Generation technology ("3G"), or Fifth Generation ("5G")/New Radio ("NR") technology. Network 108 can use any of the above radio access technologies, or any other available radio access technology, to communicate with tracking device 102, server 106, and/or mobile device 104.

In one non-limiting embodiment, the network 108 can include a WLAN, such as a wireless fidelity ("Wi-Fi") network defined by the IEEE 802.11 standards or equivalent standards. In this embodiment, network 108 can allow the transfer of location and/or any tracked or monitored data from tracking device 102 to server 106. Additionally, the network 108 can facilitate the transfer of data between tracking device 102 and mobile device 104. In an alternative embodiment, the network 108 can comprise a mobile network such as a cellular network. In this embodiment, data can be transferred between the illustrated devices in a manner similar to the embodiment wherein the network 108 is a WLAN. In certain non-limiting embodiments tracking device 102, also referred to as wearable device, can reduce network bandwidth and extend battery life by transmitting when data to server 106 only or mostly when it is connected to the WLAN network. When it is not connected to a WLAN, tracking device 102 can enter a power-save mode where it can still monitor and/or track data, but not transmit any of the collected data to server 106. This can also help to extend the battery life of tracking device 102.

In one non-limiting embodiment, tracking device 102 and mobile device 104 can transfer data directly between the devices. Such direct transfer can be referred to as device-to-device communication or mobile-to-mobile communication. While described in isolation, network 108 can include multiple networks. For example, network 108 can include a Bluetooth network that can help to facilitate transfers of data between tracking device 102 and mobile device 104, a wireless land area network, and a mobile network.

The system 100 can further include a mobile device 104. Mobile device 104 can be any available user equipment or mobile station, such as a mobile phone, a smart phone or multimedia device, or a tablet device. In alternative embodiments, mobile device 104 can be a computer, such as a laptop computer, provided with wireless communication capabilities, personal data or digital assistant (PDA) provided with wireless communication capabilities, portable media player, digital camera, pocket video camera, navigation unit provided with wireless communication capabilities or any combinations thereof. As discussed previously, mobile device 104 can communicate with a tracking device 102. In these embodiments, mobile device 104 can receive location, data related to a pet, wellness assessment, and/or health recommendation from a tracking device 102, server 106, and/or network 108. Additionally, tracking device 102 can receive data from mobile device 104, server 106, and/or network 108. In one non-limiting embodiment, tracking device 102 can receive data regarding the proximity of mobile device 104 to tracking device 102 or an identification of a user associated with mobile device 104. A user associated with mobile device 104, for example, can be an owner of the pet.

Mobile device 104 (or non-mobile device) can additionally communicate with server 106 to receive data from server 106. For example, server 106 can include one or more application servers providing a networked application or application programming interface (API). In one non-limiting embodiment, mobile device 104 can be equipped with one or more mobile or web-based applications that communicates with server 106 via an API to retrieve and present data within the application. In one non-limiting embodiment, server 106 can provide visualizations or displays of location or data received from tracking device 102. For example, visualization data can include graphs, charts, or other representations of data received from tracking device 102.

FIG. 2 illustrates a device that can be used to track and monitor a pet according to certain non-limiting embodiments. The device 200 can be, for example, tracking device 102, server 106, or mobile device 104. Device 200 includes a CPU 202, memory 204, non-volatile storage 206, sensor 208, GPS receiver 210, cellular transceiver 212, Bluetooth transceiver 216, and wireless transceiver 214. The device can include any other hardware, software, processor, memory, transceiver, and/or graphical user interface.

As discussed with respect to FIG. 2, the device 200 can a wearable device designed to be worn, or otherwise carried, by a pet. The device 200 includes one or more sensors 208, such as a three-axis accelerometer. One or more sensor 208 can be used to detect any bodily movement associated with itching, scratching, licking, walking, drinking, eating, sleeping, and shaking, and/or any other bodily movement associated with an action performed by the pet. In some non-limiting embodiments one or more sensors 208 can detect activity of a pet after or before a medical procedure, administration or medication or a pharmaceutical product, and/or a veterinary visit.

The one or more sensors can be used in combination with GPS receiver 210, for example. GPS receiver 210 can be used along with sensor 208 which monitor the device 200 to identify its position (via GPS receiver 210) and its acceleration, for example, (via sensor 208). Although illustrated as single components, sensor 208 and GPS receiver 210 can alternatively each include multiple components providing similar functionality. In certain non-limiting embodiment, GPS receiver 210 can instead be a Global Navigation Satellite System (GLONASS) receiver.

Sensor 208 and GPS receiver 210 generate data as described in more detail herein and transmits the data to other components via CPU 202. Alternatively, or in conjunction with the foregoing, sensor 208 and GPS receiver 210 can transmit data to memory 204 for short-term storage. In one non-limiting embodiment, memory 204 can comprise a random-access memory device or similar volatile storage device. Memory 204 can be, for example, any suitable storage device, such as a non-transitory computer-readable medium. A hard disk drive (HDD), random access memory (RAM), flash memory, or other suitable memory.

Alternatively, or in conjunction with the foregoing, sensor 208 and GPS receiver 210 can transmit data directly to non-volatile storage 206. In this embodiment, CPU 202 can access the data (e.g., location and/or event data) from memory 204. In some non-limiting embodiments, non-volatile storage 206 can comprise a solid-state storage device (e.g., a "flash" storage device) or a traditional storage device (e.g., a hard disk). Specifically, GPS receiver 210 can transmit location data (e.g., latitude, longitude, etc.) to CPU 202, memory 204, or non-volatile storage 206 in similar manners. In some non-limiting embodiments, CPU 202 can comprise a field programmable gate array or customized application-specific integrated circuit.

As illustrated in FIG. 2, the device 200 includes multiple network interfaces including cellular transceiver 212, wireless transceiver 214, and Bluetooth transceiver 216. Cellular transceiver 212 allows the device 200 to transmit the data, processed by CPU 202, to a server via any radio access network. Additionally, CPU 202 can determine the format and contents of data transferred using cellular transceiver 212, wireless transceiver 214, and Bluetooth transceiver 216 based upon detected network conditions. Transceivers 212, 214, 216 can each, independently, be a transmitter, a receiver, or both a transmitter and a receiver, or a unit or device that can be configured both for transmission and reception. The transmitter and/or receiver (as far as radio parts are concerned) can also be implemented as a remote radio head which is not located in the device itself, but in a mast, for example.

Figure 3:
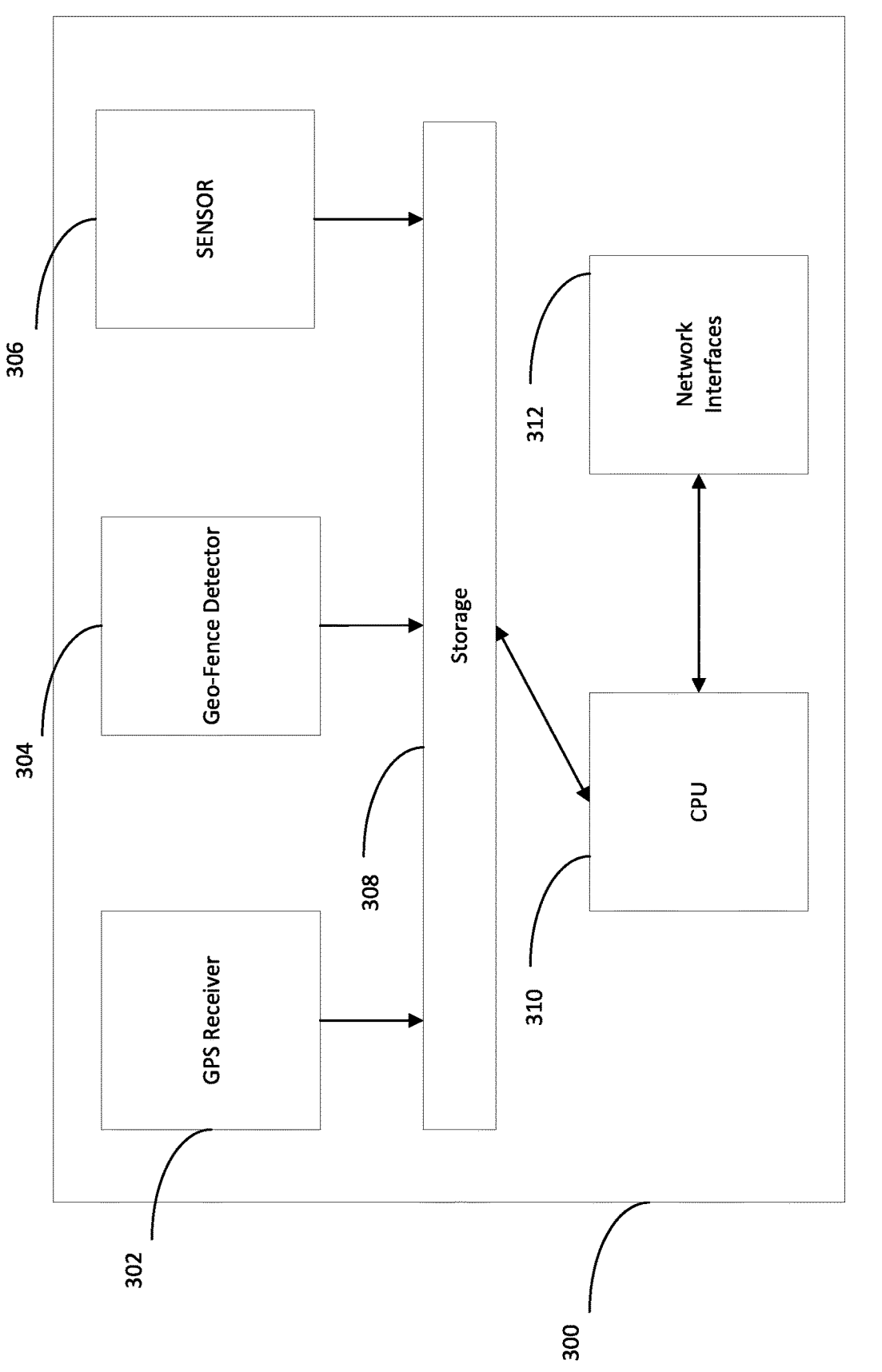
FIG. 3 illustrates a device used for pet monitoring according to certain non-limiting embodiments.

FIG. 3 illustrates a device or apparatus that can be used to track or monitor a pet according to certain non-limiting embodiments. As illustrated in FIG. 3, a device 300, such as tracking device 102 shown in FIG. 1, also referred to as a wearable device, or mobile device 104 shown in FIG. 1, which can include a GPS receiver 302, a geo-fence detector 304, a sensor 306, storage 308, CPU 310, and network interfaces 312. Geo-fence can refer a geolocation-fence as described below. GPS receiver 302, sensor 306, storage 308, and CPU 310 can be similar to GPS receiver 210, sensor 208, memory 204/non-volatile storage 206, or CPU 202, respectively. Network interfaces 312 can correspond to one or more of transceivers 212, 214, 216. Device 300 can also include one or more power sources, such as a battery. Device 300 can also include a charging port, which can be used to charge the battery. The charging port can be, for example, a type-A universal serial bus ("USB") port, a type-B USB port, a mini-USB port, a micro-USB port, or any other type of port. In some other non-limiting embodiments, the battery of device 300 can be wirelessly charged.

In certain non-limiting embodiments, GPS receiver 302 can record location data associated with device 300. Location data, for example, can includes numerous data points representing the location of the device 300 as a function of time.

In some non-limiting embodiments, geo-fence detector 304 stores details regarding known geo-fence zones. For example, geo-fence detector 304 can store a plurality of latitude and longitude points for a plurality of polygonal geo-fences. The latitude and/or longitude points or coordinates can be manually inputted by the user and/or automatically detected by the wearable device. In alternative non-limiting embodiments, geo-fence detector 304 can store the names of known WLAN network service set identifier (SSIDs) and associate each of the SSIDs with a geo-fence. In certain non-limiting embodiments, geo-fence detector 304 can store, in addition to an SSID, one or more thresholds for determining when the device 300 exits a geo-fence zone. Although illustrated as a separate component, in some non-limiting embodiments, geo-fence detector 304 can be implemented within CPU 310, for example, as a software module.

GPS receiver 302, for example, can transmit latitude and longitude data to geo-fence detector 304 via storage 308 or, alternatively, indirectly to storage 308 via CPU 310.

As illustrated in FIG. 3, device 300 further includes storage 308. In certain non-limiting embodiments, storage 308 can store past or previous data sensed or received by device 300. For example, storage 308 can store past location data. In other non-limiting embodiments, instead of storing previously sensed and/or received data, device 300 can transmit the data to a server, such as server 106 shown in FIG. 1. The sensed data can then be used to determine a health indicator which can be stored at the server. The server 106 can then compare the health indicators it has determined based on the recent data it receives to the stored health indicators, which can be based on previously stored data. For example, the sensed movement data of the pet can indicate a health indicator, such as scratching or itching performed by a pet. Based on the health indicator, a wellness assessment can be determined. The wellness assessment, for example, can indicate that a pet suffers from pruritus. In certain non-limiting embodiments, device 308 can use its own computer capabilities or hardware to determine a health indicator and/or corresponding wellness assessment.

As described above, certain non-limiting embodiments can include sensed bodily movements of a pet using one or more sensors 208. The bodily movement of a pet, for example, can be associated with itching, scratching, licking, walking, drinking, eating, sleeping, and shaking, and/or any other bodily movement associated with an action performed by the pet. Based on the bodily movement of the pet a health indicator can be determined, from which a wellness assessment can be determined. The wellness assessment, for example, can be that a pet is suffering from a dermatological ailment or issue, such as pruritus. A health recommendation can then be made using server 106 or device 308. The health recommendation, for example, can include a recommendation for one or more pet products or for a pet to be taken to a veterinarian. In certain non-limiting embodiments, pets with dermatological issues experience three times as much daily scratching as pets without any dermatological issues. While pet scratching can vary amongst breeds and based on the season, tracking health indicators such as scratching can help to determine wellness assessments, such as one or more dermatological issue(s).

CPU 310 can control access to storage 308, retrieving data from storage 308, and transmitting data to a networked device via network interfaces 312. CPU 310 can receive indications of geo-fence zone exits from geo-fence detector 304 and can communicate with a mobile device using network interfaces 312. In one non-limiting embodiment, CPU 310 can receive location data from GPS receiver 302 and can store the location data in storage 308. In certain non-limiting embodiments, storing location data can associate a timestamp with the data. In some non-limiting embodiments, CPU 310 can retrieve location data from GPS receiver 302 according to a pre-defined interval. For example, the pre-defined interval can be once every three minutes. In some non-limiting embodiments, this interval can be dynamically changed based on the estimated length of a walk or the remaining battery life of the device 300. CPU 310 can transmit location data to a remove device or location via network interfaces 312.

Figure 4:
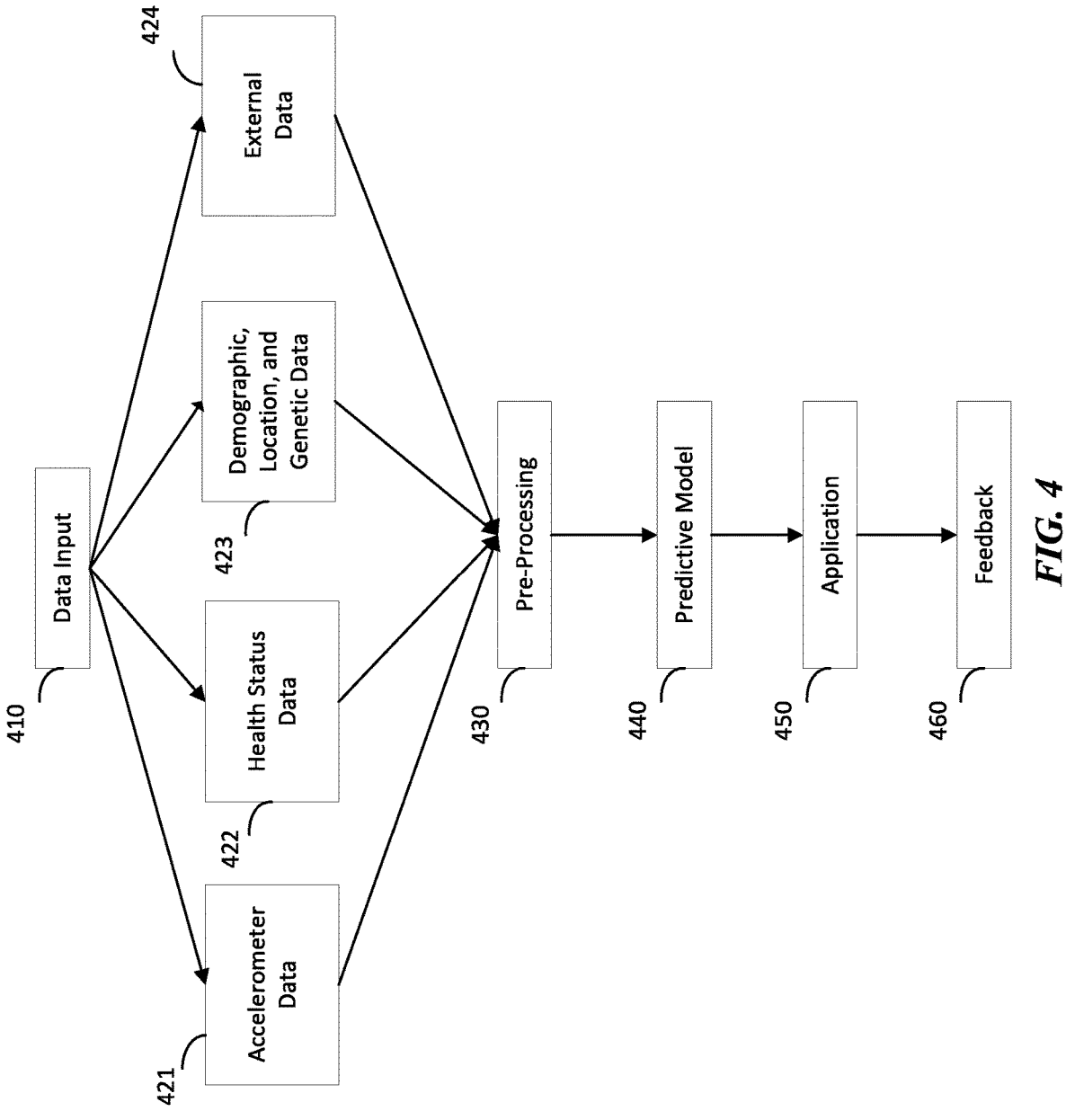
FIG. 4 illustrates a flow diagram of a method or process for performing a wellness assessment according to certain non-limiting embodiments.

FIG. 4 illustrates a flow diagram of a method or process for performing a wellness assessment of a pet according to certain non-limiting embodiments. Step 410 can include inputting data. For example, the inputted data can include, but not limited to, pet identifiers such as name, date of birth, and breed, device 102 data such as device activation rate, retention rate, and engagement, and pet activity/health data such as minutes of activity, licking frequency, scratching frequency, sleeping, eating, and drinking. The inputted data can be collected from one or more sensors 208 of tracking or wearable device 102. For example, inputted data can be collected from accelerometer 421, which can include both high-frequency data and low-frequency data. High-frequency data can be 50 Hz accelerometer data. An example use case of high-frequency data can be computing health indicators. Low-frequency data can be a representation of energy expenditure. It can be computed from the high-frequency data on the device 102. An example use case of low-frequency data can be computing mobile app features such as the activity tab in near real-time. In certain non-limiting embodiments, the inputted data can be collected from other sources. For example, health status data 422 can be inputted. Health status data 422 can include, for example, electronic medical records drawn from one or more health, clinic, or hospital records of a pet. In another example health status data 422 can be owner-reported health events. The health events, for example, can be previous episodes of pruritus.

In certain non-limiting embodiments, the one or more sensors can be associated with a wearable device worn by or attached to the first pet. For example, the inputted data can be collected from collar mounted tracking devices 102. The server 106 can detect an unwanted rotation of the wearable device. In some non-limiting embodiments, the orientation of the device 102 may not always be facing forward. For example, the device can be, and often is, rotated away from the conventional ventral (bottom) position at the lowest point of the collar. In some non-limiting embodiments, the server 106 can apply one or more transformations to the sensor data to correct the unwanted rotation. For example, transformation techniques can be used to eliminate the rotation such that the data collected from collar mounted tracking devices 102 are similar to data collected from forward facing tracking devices 120. These transformations can include using the acceleration due to gravity to help determine the location of the device around the pet's neck. Other sensors, such as gyroscopes or magnetometers can also be used in combination with filtering techniques such as a Kalman filter to help ensure accurate positioning of the device. After this location is determined, transformation matrices or quaternions can be used to mathematically transform the measurements from the sensors into a consistent coordinate system at the bottom of the pet's collar. In some non-limiting embodiments, the collar mounted tracking device can also be able to be attached to the collar in multiple orientations. The server 106 can determine an orientation of the wearable device. To account for this orientation, a machine learning model can be developed to determine the orientation of the device on the collar. This model can be trained using data collected when the device was in a known orientation on the pet's collar and be trained to predict the orientation of the device on the collar. In certain non-limiting embodiments, this machine learning model can be a convolutional neural-network and the estimates can be aggregated across time to determine a single orientation for the device during that time period. The server 106 can further process the sensor data based on the orientation of the wearable device. As a result, subsequent tasks such as determining health indicators and wellness assessment can have good insensitivity (invariance) to collar orientation or position.

In some non-limiting embodiments, pet activity data of the inputted data can be generated based on an activity recognition algorithm or model. Activities can include both postures and behaviors. Postures reflect the approximate position and energy expenditure level of the pet, while behaviors characterize the pet's dominant behavior or activity in a given moment. For example, postures can include "lie down", "sit", "stand", "walk", "vigorous", and "mixed". The activity recognition algorithm or model can be used to classify a variety of pet postures/behaviors based on sensor data (e.g., movement of a pet) collected from the sensors 208 of tracking or wearable device 102 associated with pets. In some non-limiting embodiments, the sensor 208 can be a collar mounted triaxial accelerometer, which can allow the wearable device 102 to detect various body movements of the pet. In some non-limiting embodiments, the sensor 208 can be a gyroscope. The various body movement can include, for example, any bodily movement associated with itching, scratching, licking, walking, drinking, eating, sleeping, and shaking, and/or any other bodily movement associated with an action performed by the pet. In certain examples, the sensor data can include data associated with a pet jumping around, being excited for food, eating voraciously, drinking out of the bowl on the wall, and/or walking around the room. The sensor data can also include data associated with activities of a pet after a medical procedure or veterinary visit, such as a castration or ovariohysterectomy visit. The activity recognition algorithm or model can be generated based on machine learning techniques such as feed forward networks, deep forward feed networks, deep convolutional networks, and/or long-short term memory networks. In some non-limiting embodiments, a deep learning activity recognition model can include a convolutional neural network (CNN) component. While in some examples a neural network can train a learned weight for every input-output pair, CNNs can convolve trainable fixed-length kernels or filters along their inputs. CNNs, in other words, can learn to recognize small, primitive features (low levels) and combine them in complex ways (high levels).

In an example non-limiting embodiment, the activity recognition algorithm or model can take in 50 Hz accelerometer data (50 data points per second) and outputs 3 Hz (3 predictions of activities per second). However, it may be not worth storing and analyzing predictions at such low granularity. Instead, predictions may be combined into minutely, hourly, and daily aggregations. One particular feature of probability aggregations that makes aggregations easier can be that the probabilities are normalized to their respective units of time. For example, summing 60 minutely can equal one hourly probability aggregation. In this case, the aggregations are probability-weighted time aggregations, so that they approximately represent the model's best estimate of the amount of time that each activity occurred inside the aggregated time period. This however means the probabilities can be no longer bounded between zero and one but now instead have a time dependent interpretation. Based on the aggregated probabilities, the activity recognition algorithm or model can further classify the postures or behaviors of pets. Table 1 illustrates example classification results on an experimental dataset.

TABLE 1

| Accuracy of behavior classification. | | | | | | |
|---|---|---|---|---|---|---|
| Behavior | No. dogs/videos | Sensitivity | Specificity | Accuracy | PPV | F1 Score |
| Eat | 1,101/1,442 | 0.902 | 0.967 | 0.99 | 0.915 | 0.972 |
| Drink | 752/1,019 | 0.874 | 0.995 | 0.948 | 0.870 | 0.872 |
| Lick object | 460/629 | 0.410 | 0.990 | 0.98 | 0.439 | 0.424 |
| Lick self | 257/398 | 0.772 | 0.990 | 0.982 | 0.728 | 0.749 |
| Petting | 204/307 | 0.305 | 0.991 | 0.981 | 0.237 | 0.267 |
| Rubbing | 158/235 | 0.729 | 0.996 | 0.996 | 0.584 | 0.648 |

TABLE 1-continued

| | | Accuracy of behavior classification. | | | | |
|---|---|---|---|---|---|---|
| Behavior | No. dogs/videos | Sensitivity | Specificity | Accuracy | PPV | F1 Score |
| Scratch | 158/303 | 0.870 | 0.997 | 0.997 | 0.676 | 0.761 |
| Shake | 251/435 | 0.916 | 1.000 | 1.00 | 0.795 | 0.851 |
| Sniff | 946/1,747 | 0.610 | 0.968 | 0.968 | 0.517 | 0.559 |
| None | 2,051/4,636 | 0.892 | 0.898 | 0.898 | 0.914 | 0.903 |

PPV = positive predictive value; F1 score = dataset accuracy.

In one example non-limiting embodiment, the activity recognition algorithm or model comprises one or more algorithms that can be used for sleep and off-collar detection. In certain non-limiting embodiments, the inputted data 410 can be arranged as a heat map to show daily patterns, based on which a heuristic algorithm can be applied for sleep and off-collar detection. An example process is as follows. At a first step, we can aggregate high-resolution (e.g., 3 Hz) data to minutely aggregations. The high-resolution data can comprise posture and behavior estimate output from the activity recognition algorithm or model. This step can be performed as usual and stored in a daily aggregation table. For example, rows in the table can be minutes from midnight and columns can be about 15 output classes including "lie down", "sit", "stand", "walk", "vigorous", "mixed", "eat", "drink", "lick object", "lick self", "petting", "rubbing", "scratch", "shake", and "sniff", each separated into 9 bins (each covers 1/10-th of the [0, 1] probability space, and the lowest one is ignored). All data in these aggregations can be potentially valid.

At a second step, we can begin updating weekly local aggregation entries. For each weekly aggregation that we want to calculate, we can calculate the one-week primary interval for that aggregation, and the secondary interval which is 12-hour longer on each end. We then get aggregations for the entire secondary interval. Table 2 illustrates an example update of weekly local aggregation entries.

TABLE 2

| | Example update of weekly local aggregation entries. | | |
|---|---|---|---|
| Secondary Interval Start | Primary Interval Start | Primary Interval End | Secondary Interval End |
| 2018 Mar. 18 12:00:00 (Beginning of week – 12 hours) | 2018 Mar. 19 00:00:00 (Beginning of week) | 2018 Mar. 25 23:59:59 (End of Week) | 2018 Mar. 26 11:59:59 (End of week + 12 hours) |

Primary Interval

This is the week for calculation. We can throw away all previous results for this time period and re-calculate them.

Secondary Interval

This includes extra padding to 'spin up' our algorithms (from both directions), extra coverage so that we can capture full night sleep and/or nap events, which may extend into the previous and (especially) the next day.
In the secondary (non-primary) interval, we only add events in certain cases, and we never alter the aggregations that we get from the UTC days.

At a third step, we can go from aggregation probabilities. We can clean up the aggregation data frame as follows. We can get a quasi-probability by adding up the histogram bins in each row of each behavior, weighted by the center point of the bins' intervals. Afterwards, we have just one data frame column per behavior. We can then fill the data frame with zero's wherever we don't have data (so, the index includes every minute of the secondary interval). We can further calculate an "activity index" that measures the pet's overall activity level (it can be a weighted sum of the various postures, where active postures have a greater weight).

Figure 5A:
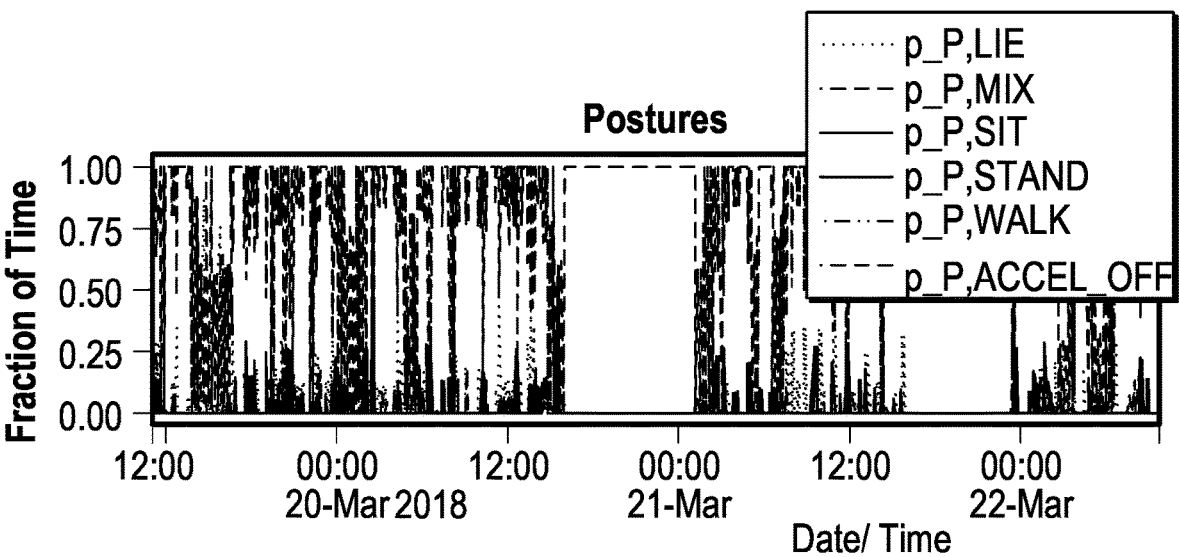
FIGS. 5A-5C illustrates example plots for the "invalid" algorithm, according to certain non-limiting embodiments.
Figure 5B:
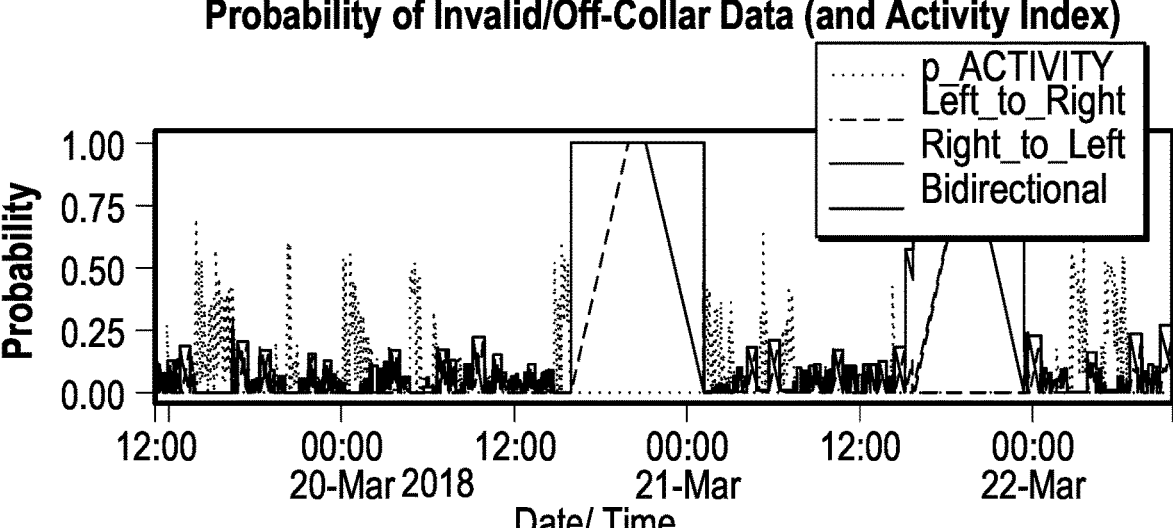
Figure 5C:
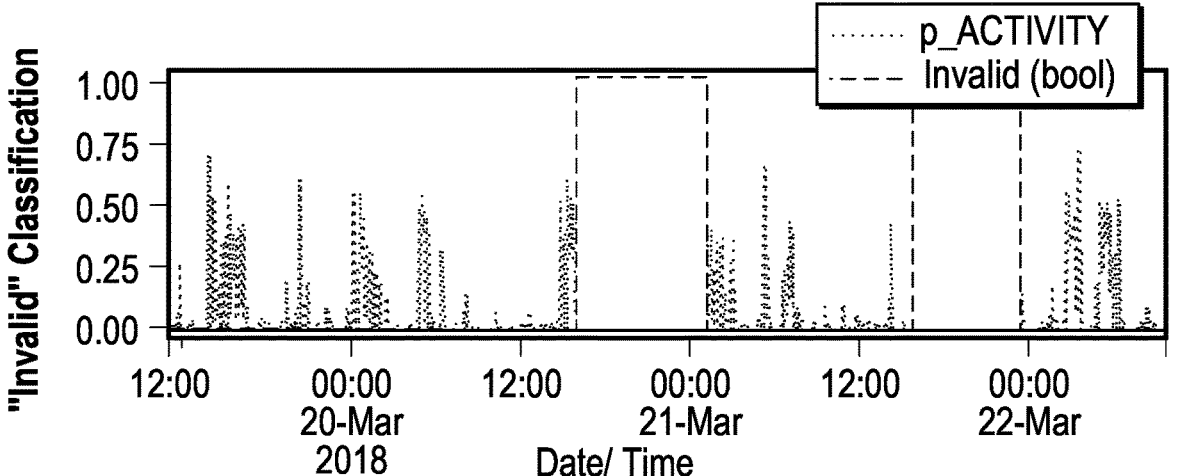

At a fourth step, an "invalid" algorithm can find invalid regions (e.g., where the tracking device 102 is off-collar). FIGS. 5A-5C illustrates example plots for the "invalid" algorithm, according to certain non-limiting embodiments. As indicated by FIG. 5A, we take the time ratios of each posture to create an activity index which corresponds to the pet's visible activity/movement level. As indicated by FIG. 5B, we then run an algorithm that accumulates probability of the signal being invalid whenever there is no activity, and that sheds that probability when it sees activity. We calibrate the algorithm so that it reaches probability of 1 in about 3 hours of complete activity. We run this algorithm both left-to-right and right-to-left. We combine the two estimates (left-to-right and right-to-left) by adding them together and capping the total at probability=1. This gives us sharp edges on the left and right sides. We threshold that signal at p=0.75 and do some morphological operations to get rid of short gaps below 20 minutes in length, and blips where the data is invalid for less than 60 minutes. As indicated by FIG. 5C, we then find those invalid regions and make a data frame describing them. The data frame can include confidence, which is the value of the bidirectional probability estimate in the masked region (e.g., for the 'invalid' algorithm, it tends to be very close to 1). The reason in the data frame can be marked as inactivity. In certain non-limiting embodiments, there can be invalid region due to the device 102 charging or, potentially, other reasons.

Figure 6A:
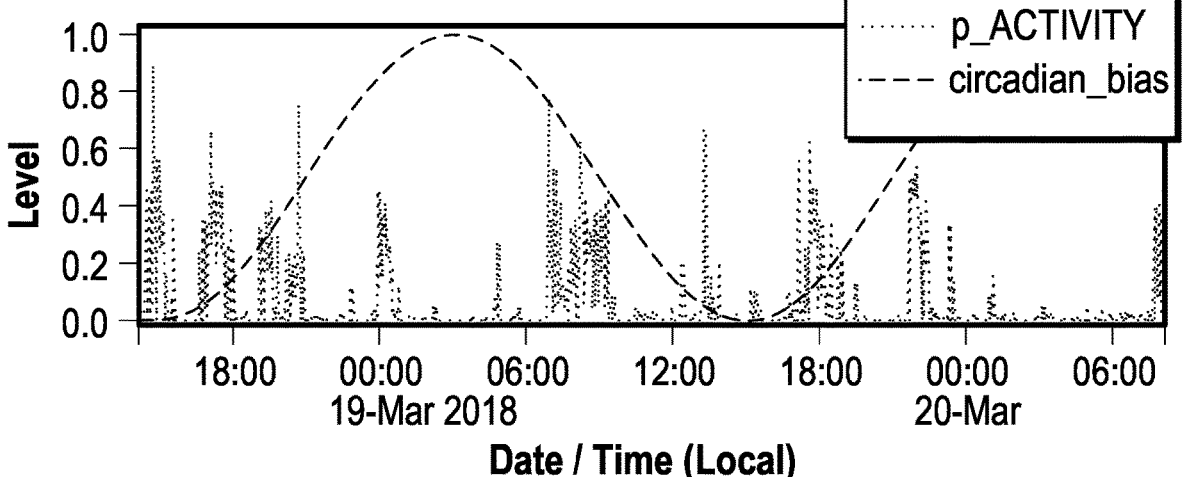
FIGS. 6A-6C illustrates example plots for using a "sleep" algorithm to find rest regions, according to certain non-limiting embodiments.
Figure 6B:
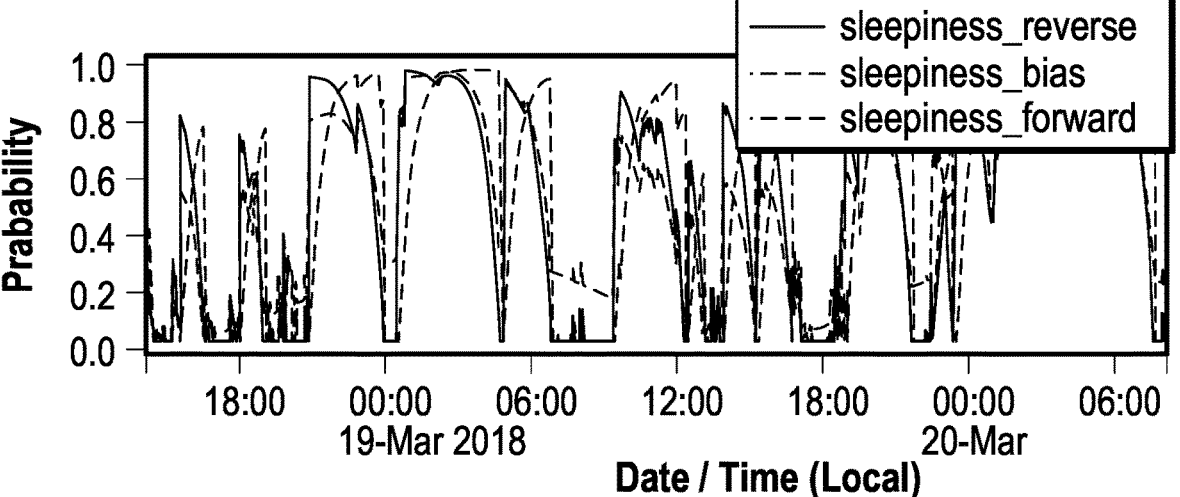
Figure 6C:
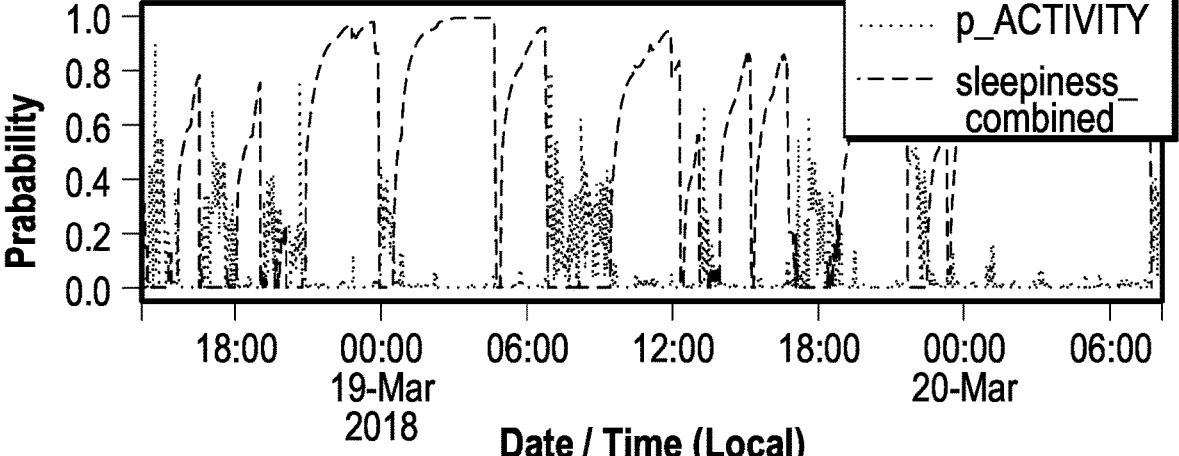

FIGS. 6A-6C illustrates example plots for using a "sleep" algorithm to find rest regions, according to certain non-limiting embodiments. The "sleep" algorithm can be similar to the "invalid" algorithm but have the following specifical considerations. Firstly, "invalid" regions have virtually no accel signals. However, sleep is often punctuated by small movements, so the algorithm has to be carefully calibrated. Secondly, we need to capture shorter naps as well as long sleep events, since pets may rest a lot throughout the day. Therefore, the algorithm needs to be more aggressive and work over shorter timescales. Thirdly, the algorithm needs to better capture sleep quality as opposed to just railing against probability=1.0 for the entire duration. As indicated by FIGS. 6A-6C, we first consider both the activity index as well as a circadian bias that roughly models the likelihood that a pet is in nighttime sleep. We then calculate a "reverse" signal, in the same way that we did the "invalid" signal as previously described, but we tune it differently (so that it spins up over about an hour instead of 3 hours and is less sensitive to movement). Unlike the "invalid" algorithm, the "sleep" algorithm can accept a "bias" argument that influences how sensitive it is to movement disruptions. When the bias is high, small movements may not cause it to shed as much probability, causing it to stay closer to 1.0. When bias is low, it may be more sensitive, causing it to drop more quickly towards 0. In this case, the circadian bias can make the estimate more likely to keep predicting sleep when the pet moves slightly at night, and more likely to predict that the pet wakes up during the day when it moves. Basically, this uses our knowledge about sleep to help the algorithm reach reasonable conclusions. In alternative embodiments, we can replace circadian bias with a probability estimate that is specific to that pet and its sleep patterns. We then calculate a "forward" signal in the same way, but this time we can use a strong "bias" signal that is approximately $\frac{2}{3}\times$(sleepiness reverse signal)$+\frac{1}{3}\times$(circadian bias). This strong bias can help the sleepiness signal to not respond to movements as long as they happen in the middle of a long period of inactivity, especially at night. Finally, we combine these two signals via a two-step process. In the first step, we add the two signals together so that there are steep edges on both sides. In the second step, we apply a shifted "minimum" filter to make sure that "sleepy" regions don't intersect with "activity" regions. This part can make sure that if a pet wakes up at 9:00 am, the sleep signal can end at exactly 9:00 am, instead of waiting until, e.g., 9:03 am when the "sleepiness" probability has adjusted.

Figure 7A:
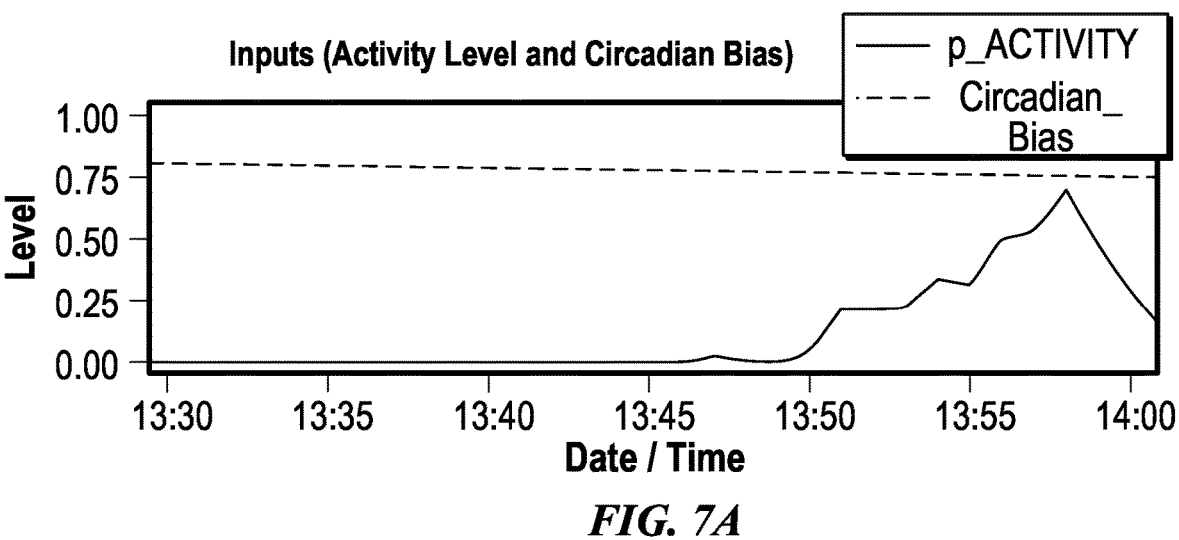
FIGS. 7A-7C illustrates example plots about half an hour of a morning wakeup period.
Figure 7B:
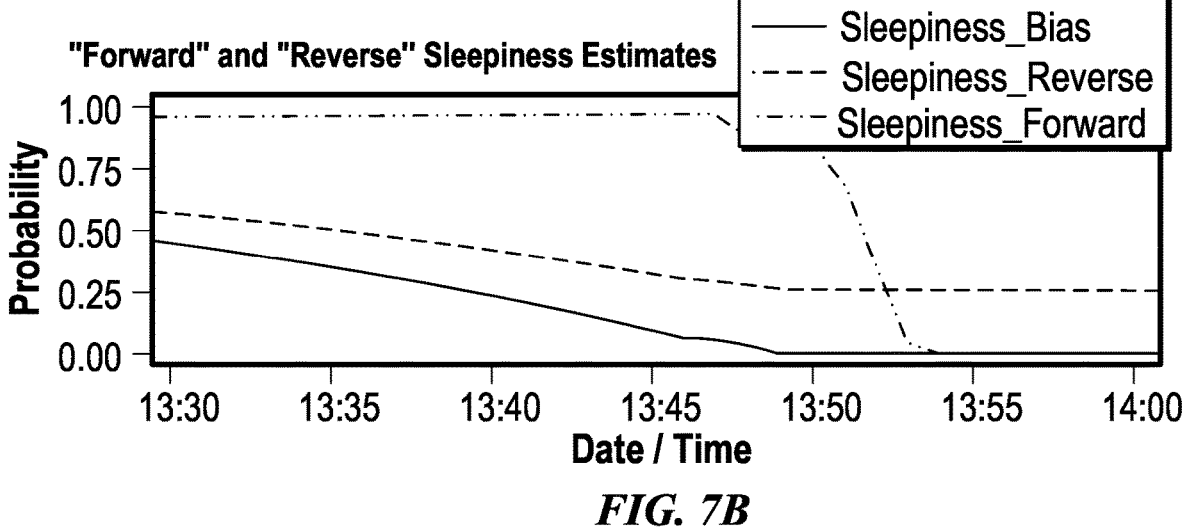
Figure 7C:
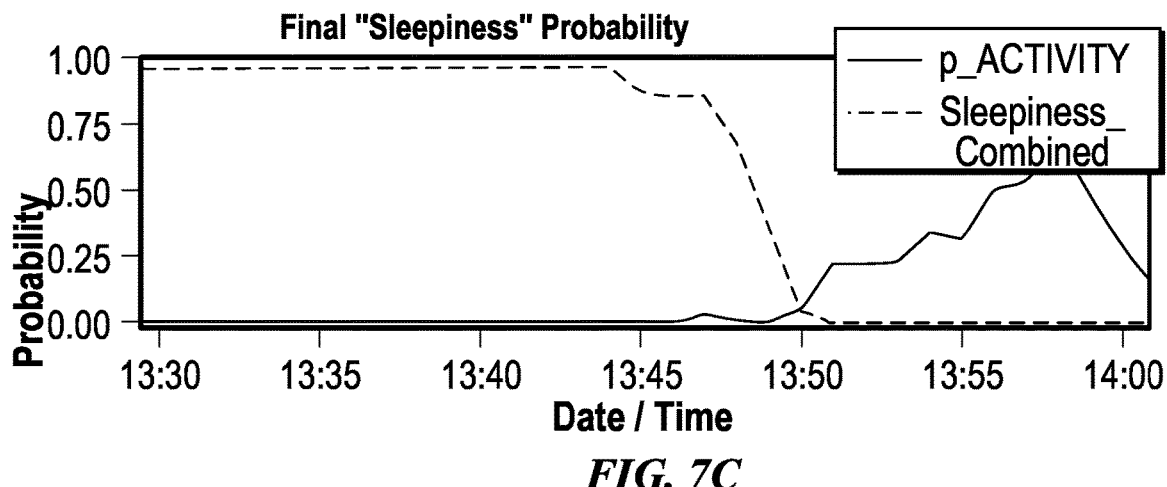

FIGS. 7A-7C illustrates example plots about half an hour of a morning wakeup period. It can be noticed that the "reverse" sleep probability is low (it hasn't had time to spin up). But the "forward" probability is correct, i.e., approximately 1.0. However, the "forward" probability extends about 10-15 minutes into when the pet has clearly woken up. The combined "sleepiness" probability (bottom plane) considers both signals, and manages to (a) realize that the pet is completely asleep until 13:45, and (b) respond almost instantly when the pet starts moving (while not overreacting to other small movements during the night). In certain non-limiting embodiments, we can implement pet-specific tuning for the "sleep" algorithm.

In certain non-limiting embodiments, we can take the "sleepiness" probability timeseries and turn it into a series of "nap" events. For example, we can do this by thresholding at p=0.5 and then by morphologically removing gaps (<6 minutes) and removing naps that are too small (<20 minutes). The result can be a "naps" data frame. The data frame can include local-time timestamps, mean and standard deviation of the "sleepiness" probability values for each nap. We can then identify nighttime sleep using an algorithm as follows. For each date in the region of interest, we can grab all nap events between 7 pm that day and 12 pm the next day. For each date in the region of interest, we can then create every possible combination of contiguous nap events. For instance, if there were naps from 7-8, 9-10, and 11-12, we can create composite naps of 7-10, 7-12, and 9-12. For each date in the region of interest, we can then score every single nap and composite nap to see how much it looks like nighttime sleep. Some of the guidelines we can use are: sleep should start between 7 pm and 2 am, preferably near 10 pm, local time; sleep should end between 4 am and noon the next day, preferably near 7 am, local time; sleep should last between 5 and 11 hours, preferably near 8 hours. For each date in the region of interest, we can then pick the best potential night sleep event and, if it's above our minimum threshold, we label it as that date's sleep event, and we remove any naps that we used to create it (if it was a composite).

We can then store all the created events (e.g., sleep, nap, and invalid) in a database. However, there is a challenge of dealing with the overlap regions since any event, but especially "sleep", can last from one aggregation period into the next. In certain non-limiting embodiments, we can address this challenge as follows. For each "sleep" event corresponding to a date in our primary interval, we can add it to the database and remove all "sleep" and "nap" events (including in the database) that intersect it. For each "nap" event, if it starts in the primary interval, we can add it and remove any intersecting "nap" events. If it starts in the secondary interval, we can add it only if it doesn't intersect any other "nap" or "sleep" events. For each "invalid" event, we can crop it to our primary interval (if needed) and add it to the database.

In certain non-limiting embodiments, other sources of inputted data can include one or more of: demographic, location, and genetic data, as shown in 423. The location, for example, can be detected using GPS receiver 302. Dog demographic information can include, for example, one or more of: age, breed, species, and gender. Dog demographic information may also include, in some embodiments, any other information of a pet. The genetic data, for example, can include one or more genetic markers, a species and/or one or more breed(s) of a pet. In some other embodiments, the inputted data can be collected from an external database or server 424. For example, the inputted data collected from an external database or server can include local weather and/or any other environmental data that can be used for wellness assessment of a pet, such a pollen count or average humidity. In some non-limiting embodiments, generating the wellness assessment of the first pet can be further based on one or more of health status data of the first pet, demographic information of the first pet, genetic data of the first pet, location of the first pet, weather information of the location of the first pet, or environment data of the location of the first pet.

Referring back to FIG. 4, the inputted data 410 can be pre-processed 430. In certain non-limiting embodiments, pre-processing 430 can include aggregating and/or time-binding predictions of pet actions, pet behaviors, and/or pet bodily movements based on data collected from one or more sensors 208 of tracking or wearable device 102. For example, pre-processing can include aggregation of scratching, itching, and/or licking by the second, minute, hour, day, month and/or year up until a labeled event. In some non-limiting embodiments, the inputted data can be labeled according to one or more of population(s), event(s), and/or time(s). For example, the population can be pets wearing tracking devices 102. The time, for example, can be the date and/or time in which a pet visits a veterinarian or in which a pet owner or other user inputs data. Similarly, the event can be a visit to a veterinarian or a pet owner or other user inputting data.

In certain non-limiting embodiments, a predictive model 440 can be used to process the pre-processed data 430. Predictive model 440 can be used to determine the health indicator and/or the wellness assessment of a pet. In some non-limiting embodiments, the health indicators comprise a metric for itching, scratching, licking, walking, drinking, eating, sleeping, and shaking. The metric can be, for example, the distance walked, time slept, and/or an amount of itching by a pet. In some non-limiting embodiments, categories can be generated for each health indicator based on its metric. For example, the categories for scratching can include infrequent, occasional, elevated, and severe. In some non-limiting embodiments, predictive model 440 can be based on one or more of the following pre-processed data: scratching seconds on the event day compared to expected baseline, self-licking seconds on the event day compared to expected baseline, average pollen counts (e.g., over a three day period) for local environment, average humidity (e.g., over a three day period) for local environment, local high temperature, local low temperature, pet age, representation of breed, presence or absence of skin-disease-related generic markers, pet breed and/or pet species (e.g., cat or dog).

Figure 8A:
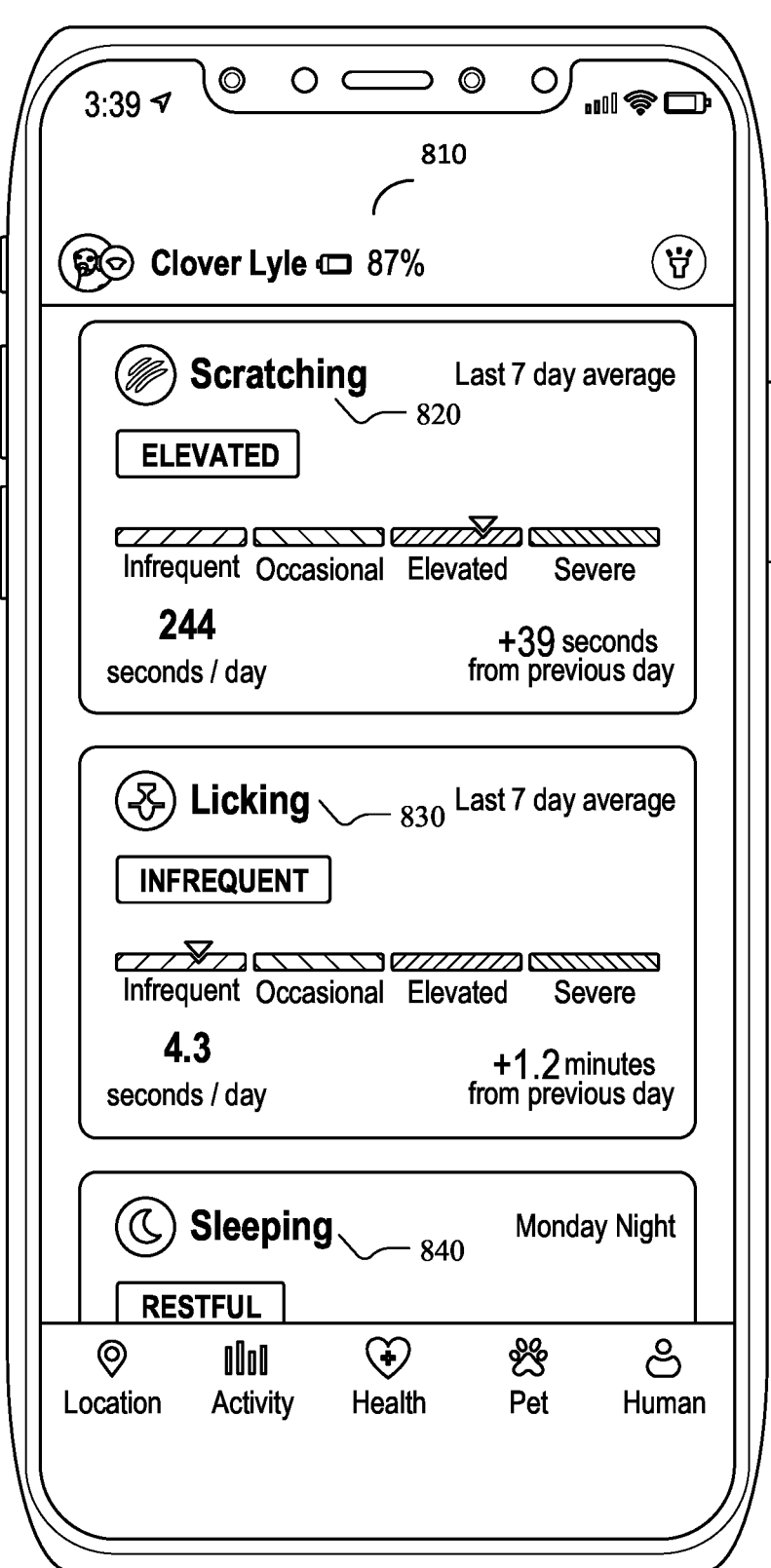
FIGS. 8A-8B illustrate examples of user interfaces displaying different health indicators according to certain non-limiting embodiments.
Figure 8B:
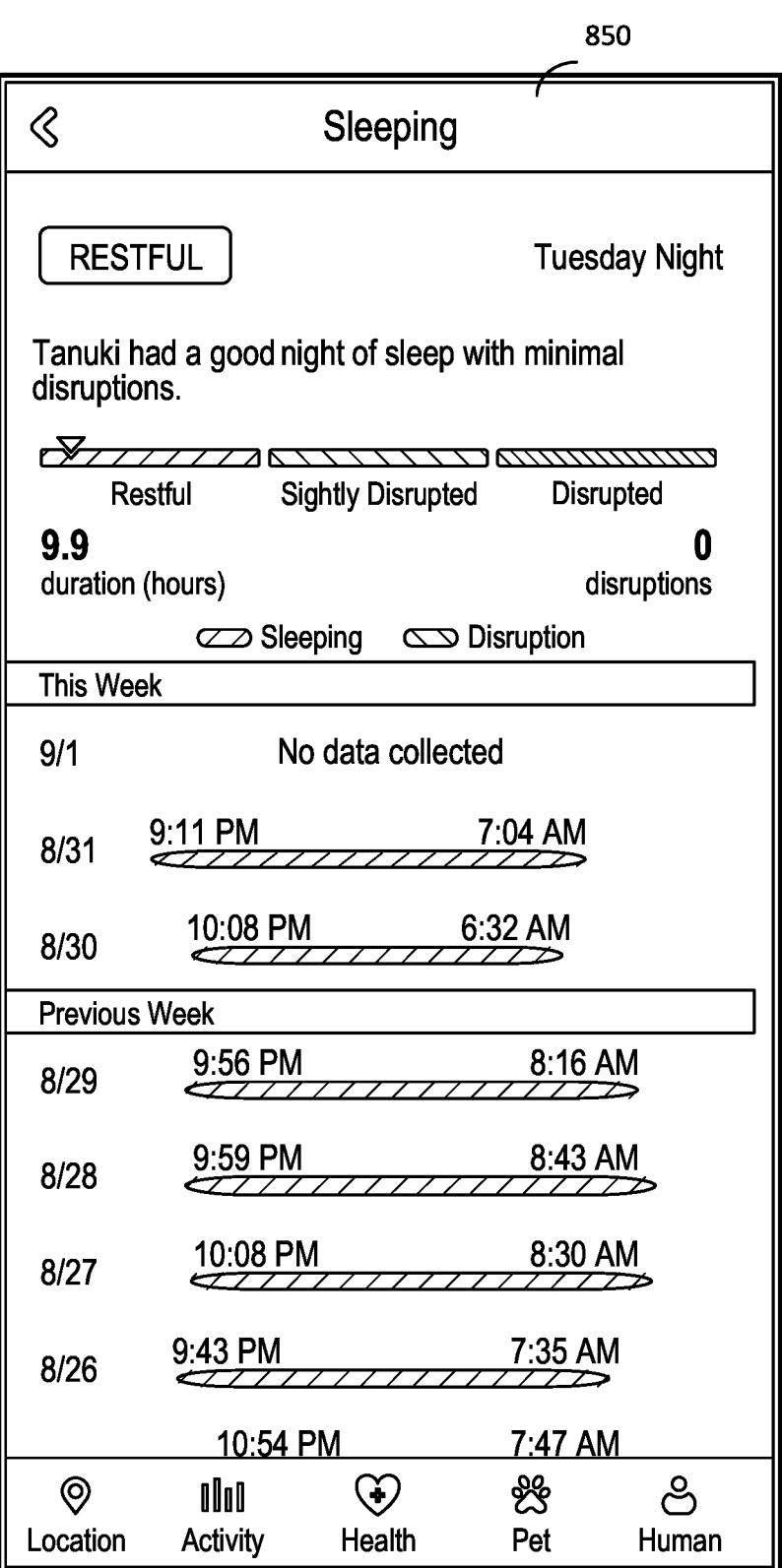

FIGS. 8A-8B illustrate examples of user interfaces displaying different health indicators according to certain non-limiting embodiments. The health indicators shown in FIG. 8A includes scratching 820, licking 830, and sleeping 840. The user interface 810 shows the category of scratching for this pet is elevated and the category of licking is infrequent, based on last 7-day average. The user interface 810 also shows the category of sleeping is restful for Monday night. In certain non-limiting embodiments, the category of sleeping (e.g., restful, slightly disrupted, and disrupted) can be determined from a sleep score. In certain non-limiting embodiments, a sleep score can be a heuristic, consumer-facing number meant to summarize sleep quality. The sleep score can be developed using population-wide sleep data, but it may have no strict quantitative link to pet health. For example, we can track 6 different variables to calculate a sleep score for a dog: the duration of sleep, the count of disruptions during the night, the total time disrupted, and then the change in each of these 3 variables against the previous week. If the user taps on the health indicator of sleeping 840, the user can be directed to a user interface 850 showing more details, as illustrated in FIG. 8B. For example, the user interface 850 shows that the pet has slept for 9.9 hours without any disruptions for Tuesday night. The user interface 850 also shows the sleeping periods for the whole week.

In certain non-limiting embodiments, the predictive model 440 can further determine a wellness assessment of the pet based on the health indicators. The wellness assessment, for example, can include an indication of one or more diseases, health conditions, and/or any combination thereof, as determined and/or suggested by the health indicators. The health conditions, for example, can include one or more of: a dermatological condition, an ear infection, arthritis, a cardiac episode, a tooth fracture, a cruciate ligament tear, a pancreatic episode and/or any combination thereof. In other non-limiting embodiments, the results of the wellness assessment can be provided by a third party, such as a veterinarian or a care giver of the pet. The wellness assessment, for example, can identify that the pet is overweight or that the pet can potentially have a disease. In certain non-limiting embodiments, the health indicator can be compared to one or more stored health indicators, which can be based on previously received data. If a threshold difference is detected by comparing the health indicator with the stored health indicator, the wellness assessment can reflect such a detection. For example, the predictive model 440 can determine that the pet is sleeping less by a given threshold, itching more by a given threshold, of eating less by a given threshold. Based on these given or preset thresholds, a wellness assessment can be performed. More information on determining health indicators and wellness assessment can be found in PCT Patent Application No. PCT/US2020/039909, filed 26 Jun. 2020, which is incorporated by reference.

Figure 9:
FIG. 9 illustrates steps of a method or process for calculating a wellness core based on activities according to certain non-limiting embodiments.
Figure 9:
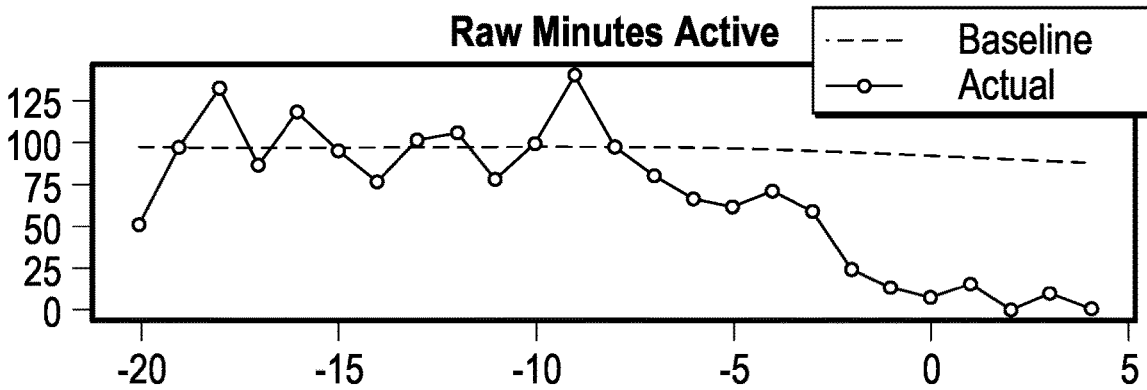
Figure 9:
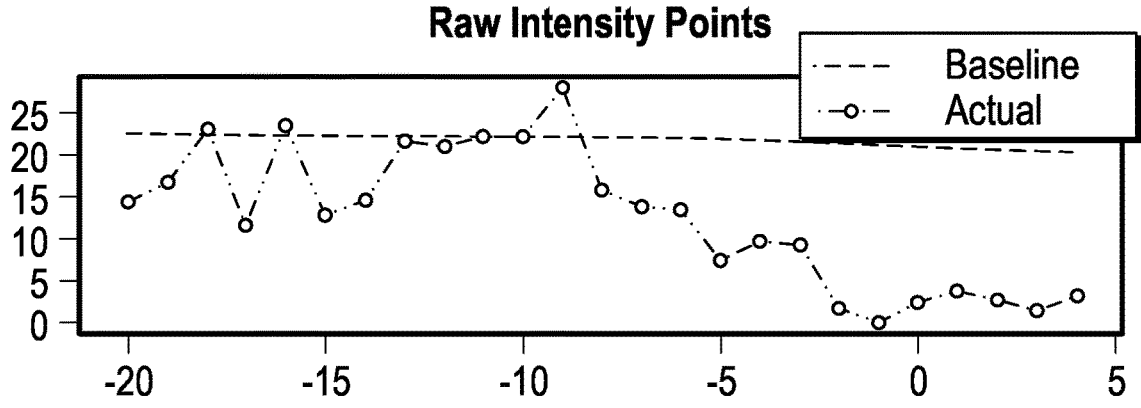
Figure 9:
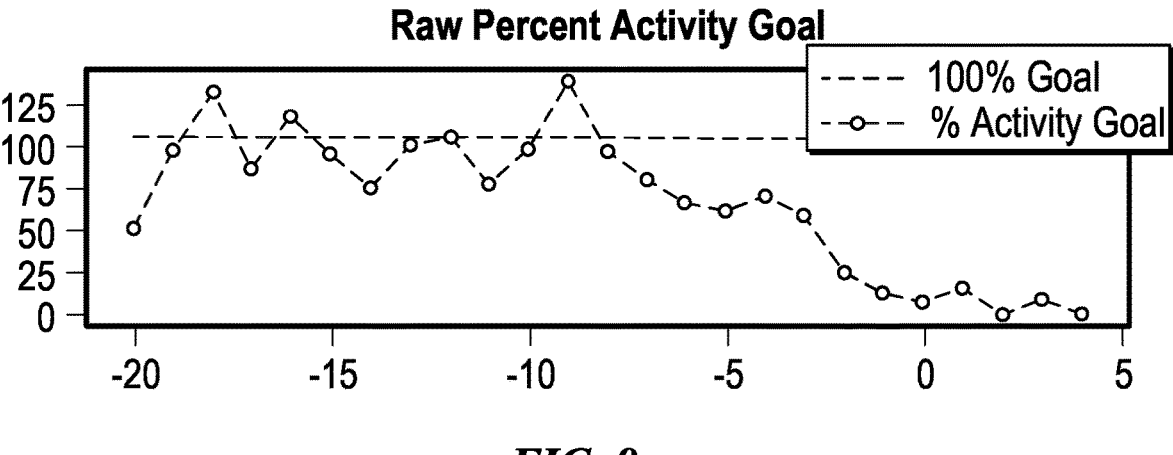
Figure 9:
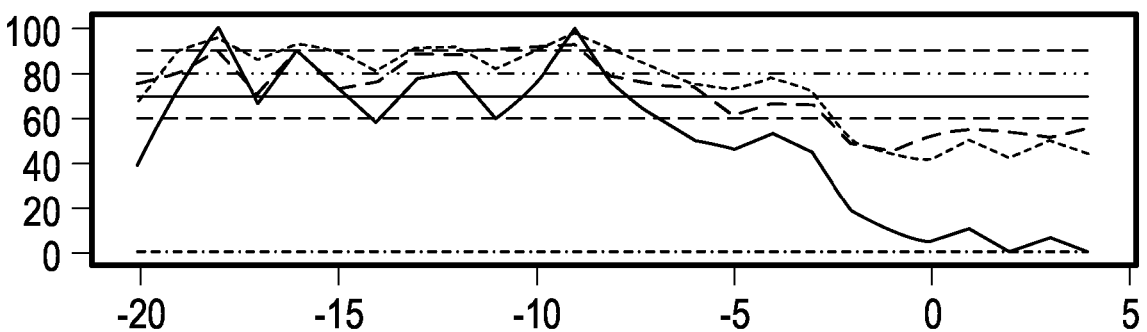
Figure 9:
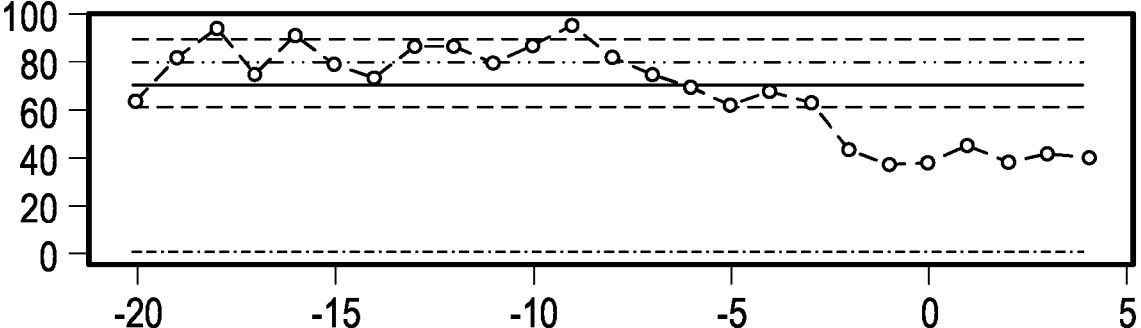

In certain non-limiting embodiments, to determine the wellness assessment of a pet, the predictive model 440 can be used to output a variety of wellness scores. For example, a wellness score can reflect the energy expenditure of a pet, which can be calculated based on one or more of an amount of time (e.g., minutes) of the first pet performing an activity, an intensity point of the first pet performing the activity, and a percentage of the amount of time of the first pet performing the activity compared to a goal time determined based on data associated with a plurality of second pets, or a percentage of the intensity point of the first pet performing the activity compared to a goal intensity point determined based on the data associated with the plurality of second pets. FIG. 9 illustrates steps of a method or process for calculating a wellness core based on activities according to certain non-limiting embodiments. The x-axis in FIG. 9 indicates days around a health event. For example, this could mean that day zero was the date of a vet visit where the pet was diagnosed with an illness and therefore day −20 would be three weeks prior to the day of the vet visit. At step 1, the predictive model 440 can determine the actual daily raw minutes of the pet being active, e.g., based on the inputted data. The baseline values for the pet being active daily can be predetermined based on observations and analyses of daily activities of similar pets (e.g., similar breed, age, weight, etc.), segmented by factors known to impact activities. The predictive model 440 can also determine the actual daily raw intensity points, e.g., based on the inputted data. The baseline values for the intensity points can be also predetermined. The predictive model 440 can further determine the daily raw percent activity goal, wherein the 100% goal can be also predetermined based on observations and analyses of daily activities of the pet in a prior 90-day range. The activity goal can be the suggested number of minutes that a pet should be active per day, determined based on knowledge of the pet. The 100% goal means the pet reached the number of set minutes. At step 2, the predictive model 440 can score each component, i.e., minutes activity score, intensity score, and percentage goal score, based on the comparisons between the daily actual values and baseline values described at step 1. At step 3, the predictive model 440 can further combine these components to generate one "activity" score. The activity score can be a component score looking only at activity metrics (e.g., raw minutes active, raw intensity points, and raw percentage of activity goal). In certain non-limiting embodiments, the activity score can be used as one component of the wellness score.

In certain non-limiting embodiments, the wellness scores can be calculated by rescaling various metrics of the health indicators into the range of 0 to 100. For example, a metric can be how long (e.g., measured in seconds) a pet scratched or licked the body. With respect to scratching, an example rescaling for generating the wellness score can be determined based on 7-day rolling average as follows. 0-52 seconds can be rescaled to a score of 90-100 indicating infrequent scratching. 52-119 seconds can be rescaled to a score of 80-90 indicating occasional scratching. 119-299 seconds can be rescaled to a score of 60-80 indicating elevated scratching. 300-600 seconds can be rescaled to a score of 0-60 indicating severe scratching. 600+ seconds can be rescaled to a score of 0. Another example rescaling for generating the wellness score for scratching can be infrequent: 0-75 seconds, occasional: 75-170 seconds, elevated: 170-360 seconds, and severe: 360+ seconds. With respect to licking, an example rescaling for generating the wellness score can be as follows. 0-420 seconds can be rescaled to a score of 90-100 indicating infrequent licking. 420-1140 seconds can be rescaled to a score of 80-90 indicating occasional licking. 1140-2580 seconds can be rescaled to a score of 60-80 indicating elevated licking. 2580-6160 seconds can be rescaled to a score of 0-60 indicating severe licking. 6160+ seconds can be rescaled to a score of 0.

Another example rescaling for generating the wellness score for licking can be infrequent: 0-15 minutes, occasional: 15-26 minutes, elevated: 26-45 minutes, and severe: 45+ minutes. The server 106 can further generate the one or more wellness scores based on the rescaled metrics.

Figure 10:
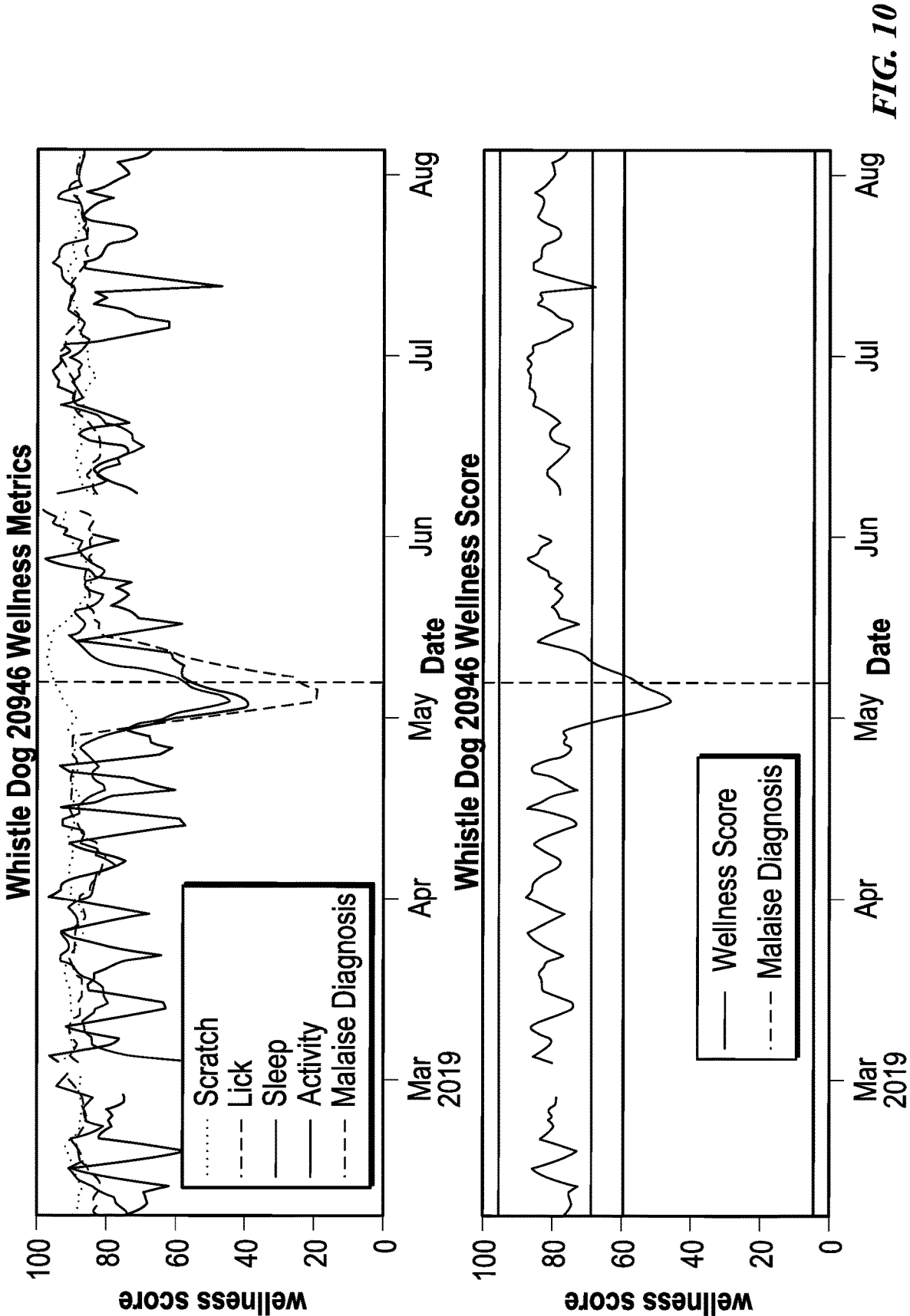
FIG. 10 illustrates an example of combined metrics for a dog that was not feeling well and visited the veterinarian.

In certain non-limiting embodiments, the one or more health indicators can be associated with one or more weights, respectively. A weight can indicate the importance of its corresponding health indicator. The predictive model 440 can additionally combine one or more metrics of one or more health indicators into one wellness score using weights and rolling averages. For example, scratching can have a weight of 0.25 and 7-day rolling average; licking can have a weight of 0.15 and 7-day rolling average; sleeping can have a weight of 0.2 and 7-day rolling average; and activity can have a weight of 0.4 and 3-day rolling average. Note here the activity indicates the general energy expenditure of a pet, mostly from walking, running, etc. The activity metric, as described previously in FIG. 9, can comprise the raw minutes active, raw intensity points, and raw percentage of activity goal. These four metrics, i.e., scratching, licking, sleeping, and activity, can be combined using geometric mean to generate one wellness score. FIG. 10 illustrates an example of combined metrics for a dog that was not feeling well and visited the veterinarian. FIG. 10 illustrates wellness scores associated with scratch, lick, sleep, and activity from before March 2019 to after August 2019. The dog had a malaise diagnosis in May. FIG. 10 also illustrates a combined wellness score. As can be seen, the combine wellness score is lowest around the time of the malaise diagnosis.

Figure 11:
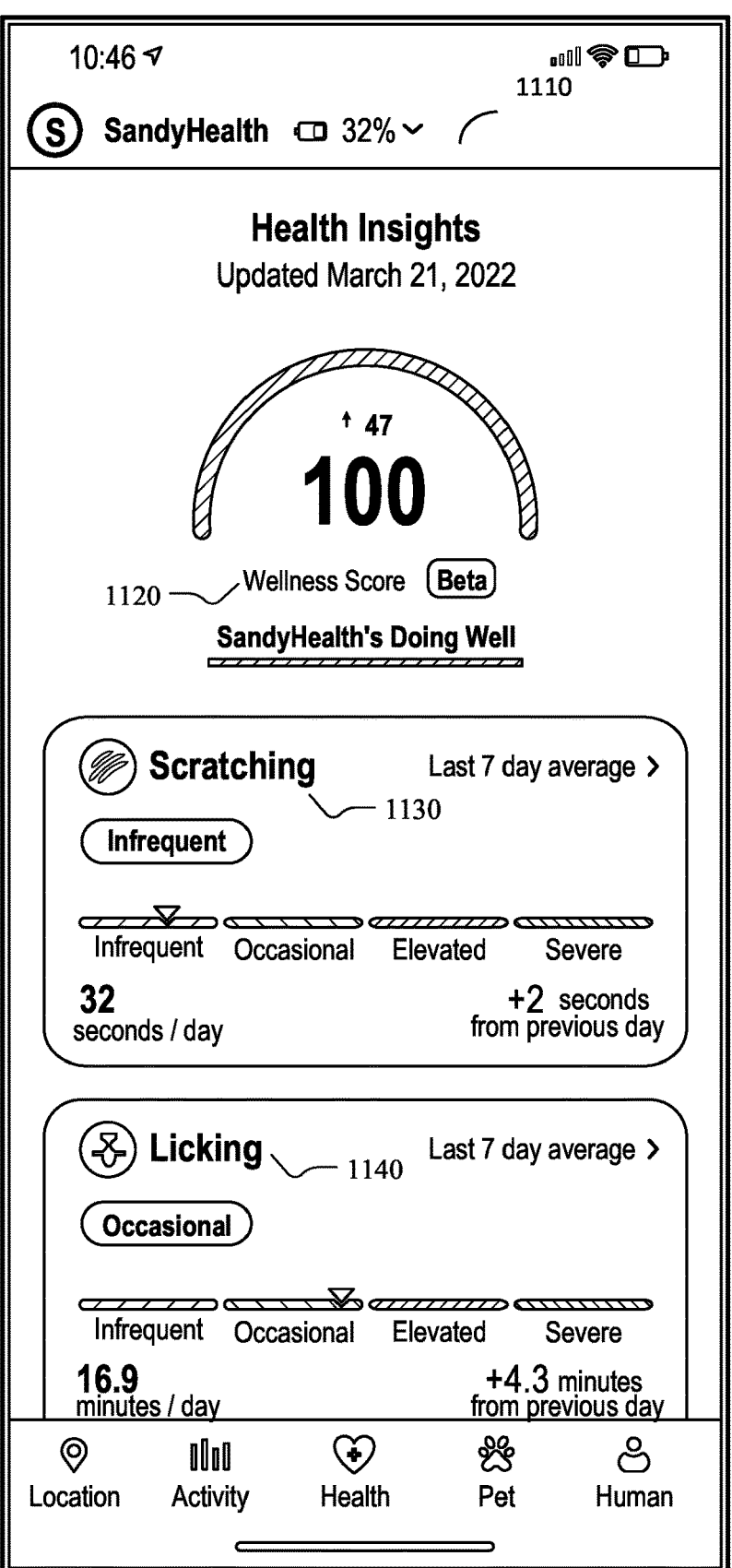
FIG. 11 illustrates an example of a user interface displaying health insights according to certain non-limiting embodiments.

FIG. 11 illustrates an example of a user interface 1110 displaying health insights according to certain non-limiting embodiments. The user interface 1110 shows that a pet's wellness score 1120 is 100, which is 47 up from previously determined wellness score. The user interface 1110 also shows the category of scratching 1130 is infrequent and the category of licking 1140 is occasional, based on last 7-day average.

Figures 12A, 12B:
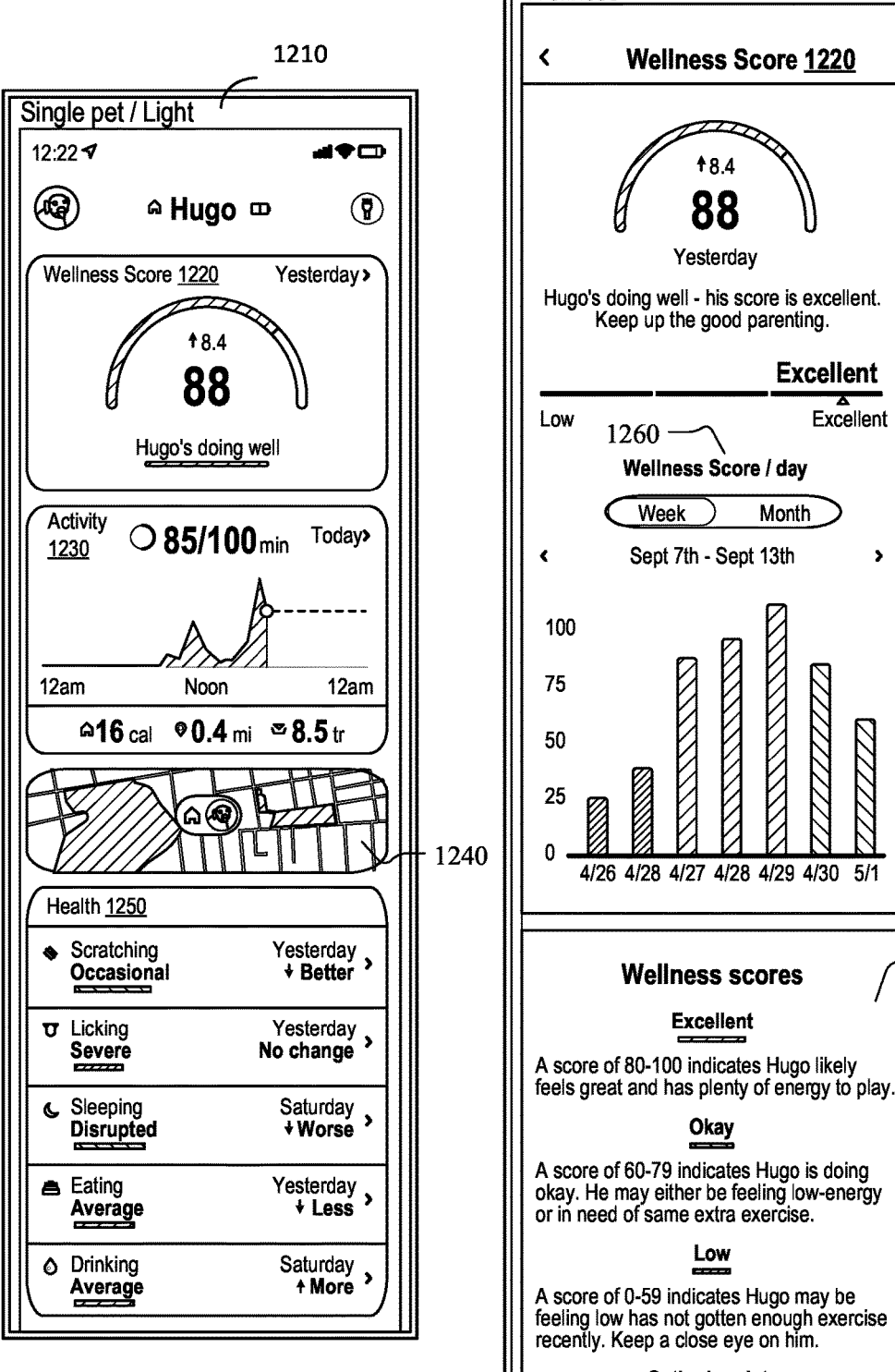
FIGS. 12A-12B illustrates an example of a home screen according to certain non-limiting embodiments.

FIGS. 12A-12B illustrates an example of a home screen 1210 according to certain non-limiting embodiments. In FIG. 12A, the home screen 1210 displays the wellness score 1220, activity 1230, location 1240, and health indicators 1250 of a pet. If a user taps on the section of wellness score 1220, the user can see further details on the wellness score 1220 and the wellness scores of the past few days 1260, which are shown in FIG. 12B. For example, the user can see the category of the wellness score 1220 (e.g., excellent) and wellness score of each day for the past week 1260. There are also explanations 1270 for different categories of wellness scores being displayed at the bottom of the interface.

In certain non-limiting embodiments, the wellness scores can be calibrated against medical records of the pet. For example, the activity score can be calibrated against medical records of sick dogs. In some embodiments, to calibrate against medical records, pets with medical records noting lethargy, malaise, or owner reported low activity can be used to benchmark what was the expected pattern of low activity around medical conditions would look like versus pets that were healthy with normal fluctuations in daily activity. As another example, the scratching and licking predictions can be calibrated against dogs with known pruritic dermatitis conditions, validated/reported against the industry standard pruritus visual analog scale (PVAS). In one embodiment, scratching and licking times can be compared to pets with known dermatologic conditions and pets with known healthy skin. This can result in the bucket scores of infrequent, occasional, elevated and severe. Pets with an infrequent evaluation could be unlikely to have a pruritic skin condition. Pets with an occasional evaluation could be normal, developing or having low-level pruritic skin condition. Pets with elevated or severe levels when evaluated by a veterinarian could be generally found to have a pruritic skin disease. The wellness scores can be compared and calibrated across a wide range of medical conditions such as dermatology, arthritis, gastrointestinal, ear infections, cardiac episode, tooth fracture, cruciate ligament tear, pancreatic episode, and malaise. These pets would have the low energy or lethargic as noted above in their medical records or would be expected to be given the diagnosis as noted above. With the calibration, the pet can be further diagnosed into actual medical conditions instead of the non-specific "I do not feel well" low-energy bucket.

In certain non-limiting embodiments, detecting the one or more activities of the first pet or determining the one or more health indicators of the first pet are based on one or more machine learning models, e.g., the activity recognition model and the predictive model 440. The one or more machine learning models can be trained based on a plurality of data associated with a plurality of second pets. In some non-limiting embodiments, the predictive model 440 can be trained to determine a health indicator and/or a wellness assessment. The prediction, for example, can be a soft classification, such as providing a relative score between 0 and 1 representing or resembling probability of disease for a pet at or over a given time and/or a given time period. To train the predictive model 440, for example, the server can aggregate data from a plurality of wearable devices 102. The aggregation of data from a plurality of wearable devices 102 can be referred to as crowd-sourcing data. The collected data from one or more pets can be aggregated and/or classified in order to learn one or more trends or relationships that exist in the data. The learned trends or relationships can be used by the server to determine, predict, and/or estimate the health indicators from the received data. The health indicators can be used for determining any behaviors exhibited by the pet, which can potentially impact the wellness or health of the pet. Machine learning can also be used to model the relationship between the health indicators and the potential impact on the health or wellness of the pet. For example, the likelihood that a pet can be suffering from an ailment or set of ailments, such as dermatological disorders can be predicted based on the health indicators. The predictive model 440 can be automated and/or semi-automated. In semi-automated models, the predictive model 440 can be assisted by a human programmer that intervenes with the automated process and helps to identify or verify one or more trends or models in the data being processed during the machine learning process.

Figure 13:
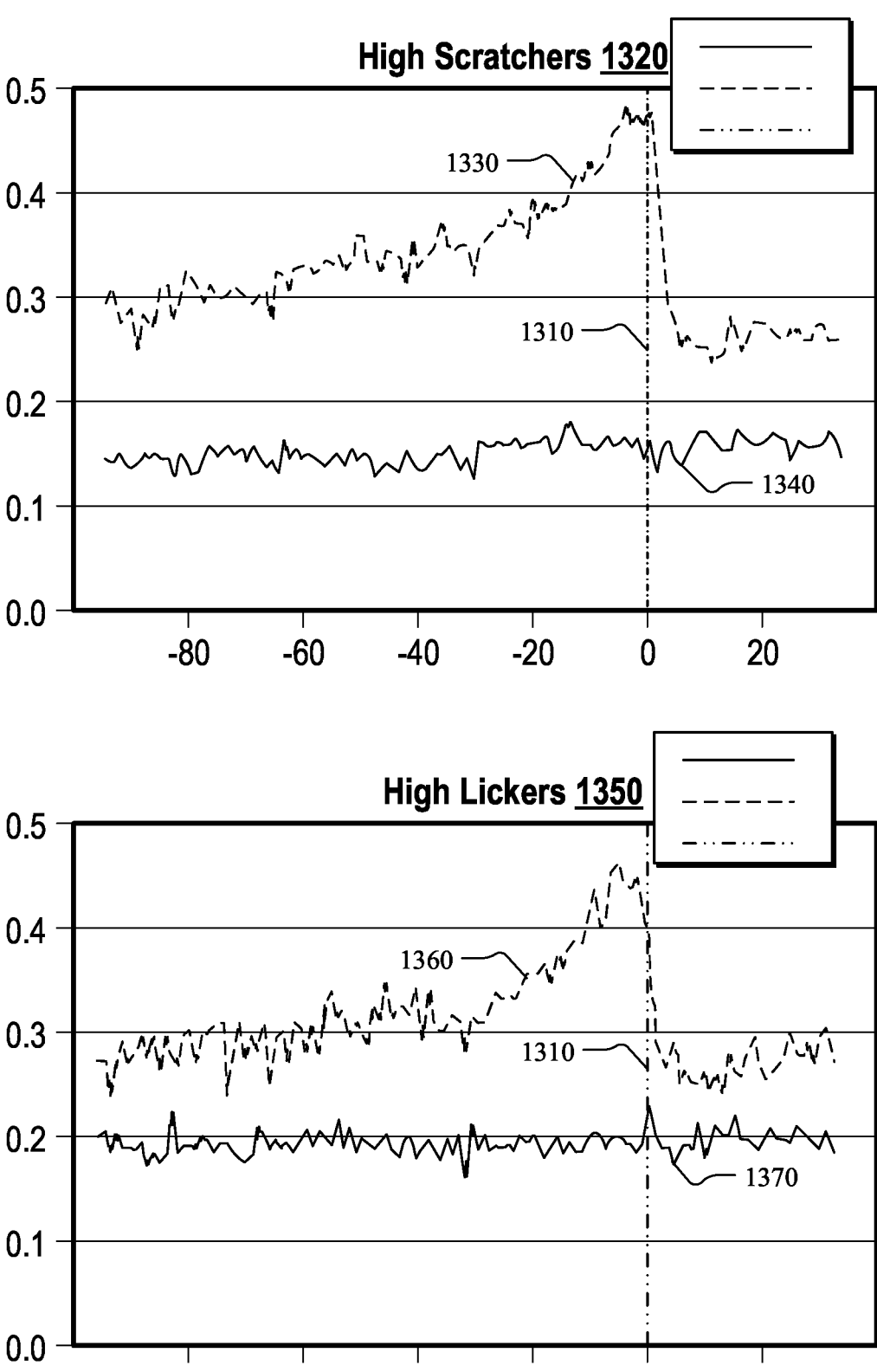
FIG. 13 illustrates an example analysis of early detection according to certain non-limiting embodiments.

As mentioned above, the predictive model 440 can be trained by harnessing the power of data. We can build the foundation to understand what is happening with pets 24/7 by collecting billions of minutes of data to train the predictive model 440. As such, the predictive model 440 can allow us to objectively understand a pet's behavior in their home environment. A better understanding of day-to-day behaviors can allow us to identify potential signs of illnesses earlier than ever before and promote earlier treatment interventions. The large amount of data can allow us to improve the accuracy of the predictive model 440 in unusual situations. The more the predictive model 440 is exposed to, the better it can be. The embodiments disclosed herein can empower pet owners with earlier awareness by lowering the burden of care for the pet owners, prevent pets from secondary infections, and helping the professionals reduce the use of antimicrobials and drug resistance. FIG. 13 illustrates an example analysis of early detection according to certain non-limiting embodiments. The x-axis in FIG. 13 indicates the days around the vet visit (which occurs at day zero). In other words, the dot line 1310 indicates the day of the vet visit. For the "high scratchers 1320", line 1330 is average scratching metric for the group with a dermatological condition and line 1340 corresponds to the control group. For the "high lickers 1350", line 1360 is average licking metric for the group with a dermatological condition and line 1370 corresponds to the control group. The analysis shows that both our scratching and licking thresholds can identify a problem for around 30% of the pets as early as 90 days before they are taken to the vet.

In certain non-limiting embodiments, the predictive model 440 can be trained using various machine learning techniques to predict or determine a health indicator and/or wellness assessment of a pet. For example, an appropriate time series can be acquired, which can be used to frame the received data. Hand-crafted statistical and/or spectral feature vectors can then be calculated over one or more finite temporal windows. A feature can be an individual measurable property or characteristic being observed via the wearable device or any other inputted data source. A feature vector can include a set of one or more features. Hand-crafted can refer to those feature vectors derived using manually predefined algorithms. A training algorithm, such as K-nearest neighbor (KNN), naïve Bayes (NB), decision trees or random forests, a boosted tree algorithm, support vector machine (SVM), or any other known training algorithms, can be further used to train the predictive model 440 such that the predictive model 440 can map the calculated feature vectors to the health indicator or wellness assessment predictions. The predictive model 440 can be evaluated on new or held-out time series data.

In certain non-limiting embodiments, one or more training algorithms can be used or integrated to improve prediction outcomes. For example, an ensemble-based method can be used to integrate one or more training algorithms when training the predictive model 440. As an example and not by way of limitation, collective of transformation-based ensembles (COTE) and the hierarchal voting variant HIVE-COTE are examples of ensemble-based methods.

Rather than using the aforementioned algorithms or techniques, such as KNN, NB, or SVM, some other embodiments can utilize one or more deep learning or neural-network models. Deep learning or neural-network models do not rely on hand-crafted feature vectors. Instead, deep learning or neural-network models use learned feature vectors derived from a training procedure. In certain non-limiting embodiments, neural networks can include computational graphs composed of many primitive building blocks, with each block performing a weighted sum of it inputs and introducing a non-linearity. In some non-limiting embodiments, a deep learning predictive model 440 can include a convolutional neural network (CNN) component. While in some examples a neural network can train a learned weight for every input-output pair, CNNs can convolve trainable fixed-length kernels or filters along their inputs. CNNs, in other words, can learn to recognize small, primitive features (low levels) and combine them in complex ways (high levels).

In certain non-limiting embodiments, pooling, padding, and/or striding can be used to reduce the size of a CNN's output in the dimensions that the convolution is performed, thereby reducing computational cost and/or making over-training less likely. Striding can describe a size or number of steps with which a filter window slides, while padding can include filling in some areas of the data with zeros to buffer the data before or after striding. Pooling, for example, can include simplifying the information collected by a convolutional layer, or any other layer, and creating a condensed version of the information contained within the layers. In some non-limiting embodiments, a one-dimensional (1-D) CNN can be used to process fixed-length time series segments produced with sliding windows. Such 1-D CNN can run in a many-to-one configuration that utilizes pooling and striding to concatenate the output of the final CNN layer. A fully connected layer can then be used to produce a class prediction at one or more time steps.

As opposed to 1-D CNNs that convolve fixed-length kernels along an input signal, recurrent neural networks (RNNs) process each time step sequentially, so that an RNN layer's final output is a function of every preceding timestep. In certain non-limiting embodiments, an RNN variant known as long short-term memory (LSTM) model can be used. LSTM can include a memory cell and/or one or more control gates to model time dependencies in long sequences. The LSTM model, for example, can be unidirectional, meaning that the model processes the time series in the order it was recorded or received. In another example, if the entire input sequence is available two parallel LSTM models can be evaluated in opposite directions, both forwards and backwards in time. The results of the two parallel LSTM models can be concatenated, forming a bidirectional LSTM (bi-LSTM) that can model temporal dependencies in both directions.

In some non-limiting embodiments, one or more CNN models and one or more LSTM models can be combined. The combined model can include a stack of four unstrided CNN layers, which can be followed by two LSTM layers and a softmax classifier. A softmax classifier can normalize a probability distribution that includes a number of probabilities proportional to the exponentials of the input. The input signals to the CNNs, for example, are not padded, so that even though the layers are unstrided, each CNN layer shortens the time series by several samples. The LSTM layers are unidirectional, and so the softmax classification corresponding to the final LSTM output can be used in training and evaluation, as well as in reassembling the output time series from the sliding window segments. The combined model though can operate in a many-to-one configuration.

The one or more models, according to some non-limiting embodiments, can be used to simultaneously calculate multiple independent outputs. For example, the same network can be used to simultaneously predict both a quickly varying behavior and a slowly varying posture. The loss functions for the multiple outputs can be simply added together, and the network can be trained on both simultaneously. This can allow a degree of automatic transfer learning between the two label sets. In certain non-limiting embodiments, transfer learning may allow us to transfer the prediction model 440 trained based on a first type of device 200 to a second type of device 200 (e.g., a new device) that may have different form factors from the first type of device 200. As a result, the wellness score can be generated based on a multi-model, multi-device architecture.

In certain non-limiting embodiments, the predictive model 440 used to map the data, such as time series accelerometer readings, into predicted health indicators can use windowed methods that predict behaviors for small windows of time. Such embodiments can produce a single prediction per window. On the other hand, in other non-limiting embodiments rather than using small windows of time, and data included therein, the predictive model 440 can run on an aggregated amount of data. The data received from the wearable device 102 can be aggregated before it can be fed into the predictive model 440, thereby allowing an analysis of a great number of data points. The aggregation of data, for example, can break the data points which are originally received at a frequency window of 3 hertz, into minutes of an hour, hour of a day, day of week, month of year, or any other periodicity that can ease the processing and help the modeling of the machine learning tool. When the data is aggregated more than once, there can be a hierarchy established on the data aggregation. The hierarchy can be based on the periodicity of the data bins in which the aggregated data are placed, with each reaggregation of the data reducing the number of bins into which the data can be placed.

For example, 720 data points, which in some non-limiting embodiments would be processed individually using small time windows, can be aggregated into 10 data points for processing by the predictive model 440. In further examples, the aggregated data can be reaggregated into a smaller number of bins to help further reduce the number data points to be processed by the predictive model 440. By running on an aggregated amount of data can help to produce a large number of matchings and/or predictions. The other non-limiting embodiments can learn and model trends in a more efficient manner, reducing the amount of time needed for processing and improving accuracy. The aggregation hierarchy described above can also help to reduce the amount of storage. Rather than storing raw data or data that is lower in the aggregation hierarchy, certain non-limiting embodiments can store data in a high aggregation hierarchy format.

In some other embodiments, the aggregation can occur after the predictive model 440 using the neural network, with the data merely being resampled, filtered, and/or transformed before it is processed by the predictive model 440. The filtering can include removing interference, such as brown noise or white noise. The resampling can include stretching or compressing the data, while the transformation can include flipping the axes of the received data. The transformation can also exploit natural symmetry of the data signals, such as left/right symmetry and different collar positions. In some non-limiting embodiments, data augmentation can include adding noise to the signal, such as brown, pink, or white noise.

Certain non-limiting embodiments can be used to determine multi-label classification and regression problems by changing the output types, such as changing the final activation function from softmax to sigmoid or linear, and/or the loss functions from cross-entropy to binary cross-entropy or mean squared error. In some examples the independent outputs in the same model can be combined. Further, one or more other layers can be added in certain non-limiting embodiments. Certain other embodiments can help to improve the layer modules by using skip connections or even a heterogeneous inception-like architecture. In addition, some non-limiting embodiments can be extended to real-time or streaming applications by, for example, using only CNNs or by replacing bidirectional LSTMs with uni-directional LSTMs.

Referring back again to FIG. 4, application 450 can be used to show a pet owner the results of the wellness assessment based on predictive model 440. Application 450 can be, for example, a mobile application. The mobile application can operate on a mobile device 104. Mobile device 104, for example, can include one or more processors, one or more memories, and/or a graphical user interface. In some non-limiting embodiments, the wellness assessment can be displayed as an alert or notification on the graphical user interface of mobile device 104. For example, the wellness assessment alert or notification can take the form of a short message service (SMS) text message, electronic mail, notification from or in the mobile application, the mobile application showing one or more of a current alert status and/or a historical alert status, and/or a notification on a separate online portal used by the pet owner or a third party. The alert or notification can be illustrated as a wellness tracking dashboard. In some non-limiting embodiments, alerts can be generated when a pet's behavior has changed categories. More specifically, alerts can be generated based on the 7-day rolling average of the daily values for different health indicators such as scratching and licking. Alerts can be generated whenever a pet crosses the predetermined threshold, in other words, changing categories. For example, an alert can be generated when a dog changed from infrequent self-licking to occasional/elevated/severe self-licking or from occasional self-licking to elevated/severe self-licking. As another example, an alert can be generated when a dog changed from infrequent scratching to occasional/elevated/severe scratching or from occasional scratching to elevated/severe scratching.

To analyze the impact of alerts, the embodiments disclosed herein present a study on 6,617 dogs with respect to dermatitis. The dogs included in the study had activities for 10-month pre-alert period and 10-month post-alert period. The activities may be sporadic in both periods, reflective of normal use. Dermatitis categories were assigned based on pre-alert period appointments that involved a dermatitis outcome. The dermatitis categories are defined as undetected pruritus (no veterinary visits with a dermatitis outcome in 10-month pre-alert period), acute (one veterinary visit with a dermatitis outcome in 10-month pre-alert period), seasonal (two to five veterinary visits with a dermatitis outcome in 10-month pre-alert period), and chronic (six or more veterinary visits with a dermatitis outcome in 10-month pre-alert period). To classify an appointment as having a dermatitis outcome, we considered visit reason (e.g., examination and coat/skin) and ailment outcomes (e.g., dermatitis, pruritus, and fleas). The veterinary visit data includes all visits related to the specific visit reasons, as well as the outcomes of those visits. A visit was considered to have a dermatitis outcome if the visit resulted in an assigned ailment in our specified list. The study shows that for dogs that were scratching before the alerts, the predictive model 440 could detect scratching even if it was not visible to the pet owners in the application 450 and no alerts were generated previously. As higher scratching and licking status are more likely to drive visit behavior, we could see increases in visits in all elevated categories as scratching and licking increases were reported to pet owners. The most notable change in visits are for dogs that did not have a dermatitis visit in the 10-month pre-alert period. They only had routine visits and were not diagnosed with any dermatologic conditions. These dogs were scratching as detected by the predictive model 440 but did not receive a diagnosis related to pruritus before pet owners were alerted to increases in scratching or licking. As a result, pet owners are equipped with a better history and knowledge of what is happening with their dogs. In partnership with their veterinarian, these dogs can receive better treatment.

Besides showing the results of the wellness assessment, the application 450 can help a pet owner with the following tasks. The application 450 can enable the pet owner to set up personalized activity goals to support an active lifestyle for their pet to keep them in peak shape. The pet owner can use the application 450 to track daily status of the pet, e.g., seeing calories burned, hours spent resting, and more. The application 450 can also have a nutrition calculator, which determines the correct amount of food based on their profile and food. The application 450 can enable the pet owner to do real-time tracking to find their lost pet fast. When the pet owner checks the health insights on the application 450, the pet owner can send the health insights of the pet to a vet so the vet can see and analyze critical behavior. The pet owner can chat, call, video call, or email with the vet via the application 450. Furthermore, the pet owner can use the application 450 to easily set reminders to help them stay on top of a healthy schedule.

In certain non-limiting embodiments, the server 106 can send, to the user device (e.g., the mobile device 104), instructions for presenting a survey or questionnaire corresponding to the wellness assessment of the first pet. In response to the alert or notification, feedback 460 can be requested from the pet owner or a third party receiving the notification. In some non-limiting embodiments, feedback 460 can be solicited when the wellness score is greater than a predetermined threshold or lower than a predetermined threshold. The solicited feedback 460, for example, can be a hyperlink to a web-based survey or questionnaire sent to a user via a SMS text message or electronic mail, a survey sent to a pet owner directly via an electronic mail, an application notification directing the pet owner to a web-based survey, a survey located within the mobile application, and/or a survey in a separate portal outside the mobile application. The feedback 460 from the pet owner can be used during pre-processing 430, to train predictive model 440, and/or to determine or predict a health indicator or a wellness assessment. In some non-limiting embodiments, the server 106 can update the one or more machine learning models based on the feedback from the user. For instance, the feedback from the pet owner can provide a True/False label for use in training a machine learning model, wherein the device's 102 sensor data provides the "features" as input to the model, and the pet owner's response provides the "target" value for optimizing the model.

In certain non-limiting embodiments, the survey or questionnaire can take the form of a pruritus visual analog scale (PVAS). The PVAS measures the itching level of a pet, such as a dog, during a 24-hour time period. The scale ranges from 0 to 10 or 0 to 100, with 0 being not itchy, meaning no scratching, chewing, rubbing, or licking observed, and 10 or 100 being extremely itchy, meaning scratching, chewing, rubbing, or licking consistent. Extreme itching, in some non-limiting embodiments, can disrupt a pet's sleeping, eating, playing, and/or exercising. The results of the PVAS survey or questionnaire can be used to confirm the determined health indicator or wellness assessment of a pet using the one or more models described above.

For example, the accuracy of predictive model 440 can be confirmed using a logistic or linear regression model with a Gaussian or beta distribution and/or logit link can be used. The model can also utilize pseudo-likelihood estimation and Kenward-Roger degrees of freedom estimation. The one or more independent variable can include scratching categories (modeled in quartiles or scratching "bucket" scores, modeled in separate models) and the one or more dependent variable can include PVAS modeled as a continuous proportion. Pair-wise comparisons among scratching categories can be adjusted for multiple comparisons using the Tukey-Kramer method.

As shown in Tables 3-5 below, as scratching severity increased as measured by the tracking device 102 and/or server 160, PVAS scores significantly ($P<0.01$) increased. On average, dogs experiencing infrequent scratching (0 to 52 sec) were described as having mild itching based on PVAS (mean score=30.4, 95% CI=26.1-35.1), whereas dogs experiencing occasional (53 to 119 sec), elevated (120 to 299 sec) or severe (>300 sec) scratching as per tracking device 102 and/or server 160 measurements, were assigned a moderate PVAS itching score (mean scores=42.2 (95% CI=38.3-46.3), 48.9 (44.5-53.3), and 52.8 (43.4-62.0), respectively) by pet owners. Accordingly, the tracking device 102 and/or server 106 employing predictive model 440 can provide a practical tool to evaluate pruritus severity. Table 3 below illustrates the results of comparing the PVAS scores entered by pet owners versus the tracking device 102 and/or server 160 measurements.

TABLE 3

Descriptive statistics and frequency tables for measurements obtained from the first and second questionnaire.

| Variable | n | mean | median | SD | Q25 | Q75 | Q90 | min-max |
|---|---|---|---|---|---|---|---|---|
| Pvas_score_1 | 358 | 45.2 | 50 | 22.8 | 30 | 63 | 71 | 0-93 |
| Scratching_seconds_1 | 358 | 137.2 | 98 | 170.0 | 57 | 171 | 265 | 1-2,271 |
| Pvas_score_2 | 358 | 41.2 | 47 | 21.6 | 21 | 57 | 66 | 0-84 |
| Scratching_seconds_1 | 358 | 152.0 | 118 | 160.9 | 57 | 188 | 299 | 1-1,346 |

| Variable | n | % |
|---|---|---|
| Scratching_score_1 | | |
| 0 - Infrequent (0-52 s) | 86 | 24.0 |
| 1 - Occasional (53-199 s) | 132 | 36.9 |
| 2 - Elevated (120-299 s) | 115 | 32.1 |
| 3 - Severe (>= 300) | 25 | 7.0 |
| Scratching_score_2 | | |
| 0 - Infrequent (0-52 s) | 87 | 24.3 |
| 1 - Occasional (53-199 s) | 94 | 26.3 |
| 2 - Elevated (120-299 s) | 142 | 39.7 |
| 3 - Severe (>=300) | 35 | 9.7 |

In certain non-limiting embodiments, Tables 4 and 5 depict unconditional associations between scratching categories (in quartiles, or based on "bucket" categories, modeled separately) with PVAS scores obtained from the first and second survey or questionnaires, respectively. Model adjusted mean PVAS scores by scratching categories were obtained from logistic regression models (using a beta distribution and logit link). Akaike and Bayesian information criteria were included for all models to be used in model selection. Lower values of the criteria can be considered better (based on this for measurements obtained from the first questionnaire, the model with scratching in quartiles is superior). For measurements obtained from the second questionnaire, both models are considered adequate as Akaike information criteria (AIC) and Bayesian information criteria (BIC) do not differ substantially (<10).

TABLE 4

Unconditional associations between scratching categories (in quartiles, and in "bucket" scores, modeled separately) with PVAS scores obtained from the second questionnaire.

| Variable, units | n | PVAS scores Q1 | | | |
|---|---|---|---|---|---|
| | | Mean score[1] | Mean score 95% CI | P-value[2] | AIC BIC |
| Scratching (in quartiles Q1) | | | | <0.001 | −120.02 |
| 1 - 1-56 s | 89 | 29.4[a] | 25.4-33.7 | | −100.62 |
| 2 - 57-97 s | 56 | 28.2[a] | 23.4-33.6 | | |
| 3 - 98-170 s | 123 | 50.6[b] | 46.5-54.6 | | |
| 4 - 171-2,271 s | 90 | 52.8[b] | 48.1-57.5 | | |
| Scratching (in "bucket" scores Q1) | | | | <0.001 | −74.49 |
| 0 - Infrequent (0-52 s) | 86 | 30.4[a] | 26.1-35.1 | | −55.09 |
| 1 - Occasional (53-199 s) | 132 | 42.2[b] | 38.3-46.3 | | |
| 2 - Elevated (120-299 s) | 115 | 48.9[b] | 44.5-53.3 | | |
| 3 - Severe (>=300 s) | 25 | 52.8[b] | 43.4-62.0 | | | n = number of observations,
CI = Confidence Interval,
AIC-BIC = Akaike Information and Bayesian Information Criteria.
[1]Significant (P < 0.05) differences in PVAS scores between scratching categories are depicted by different letter superscripts (P-values adjusted using the Tukey-Kramer method).
[2]Overall significance of variable (Wald test).

TABLE 5

Unconditional associations between scratching categories (in quartiles, and in "bucket" scores, modeled separately) with PVAS scores obtained from the second questionnaire.

| Variable, unit | n | PVAS scores Q2 | | | |
|---|---|---|---|---|---|
| | | Mean score[1] | Mean score 95% CI | P-value[2] | AIC BIC |
| Scratching (in quartiles Q2) | | | | <0.001 | −156.78 |
| 1 - 1-55 s | 89 | 23.6[a] | 20.2-27.4 | | −137.38 |
| 2 - 56-117 s | 89 | 43.8[bc] | 39.3-48.3 | | |
| 3 - 118-187 s | 73 | 39.6[b] | 34.9-44.5 | | |
| 4 - 188-1,346 s | 107 | 48.5[c] | 44.4-52.7 | | |
| Scratching (in "bucket" scores Q2) | | | | <0.001 | −152.99 |
| 0 - Infrequent (0-52 s) | 87 | 23.4[a] | 19.9-27.2 | | −133.59 |
| 1 - Occasional (53-199 s) | 94 | 43.6[b] | 39.3-48.0 | | |
| 2 - Elevated (120-299 s) | 142 | 43.9[b] | 40.3-47.5 | | |
| 3 - Severe (>=300) | 35 | 49.4[b] | 42.2-56.6 | | | n = number of observations,
CI = Confidence Interval,
AIC-BIC = Akaike Information and Bayesian Information Criteria.
[1]Significant (P < 0.05) differences in PVAS scores between scratching categories are depicted by different letter superscripts (P-values adjusted using the Tukey-Kramer method).
[2]Overall significance of variable (Wald test).

Figure 14:
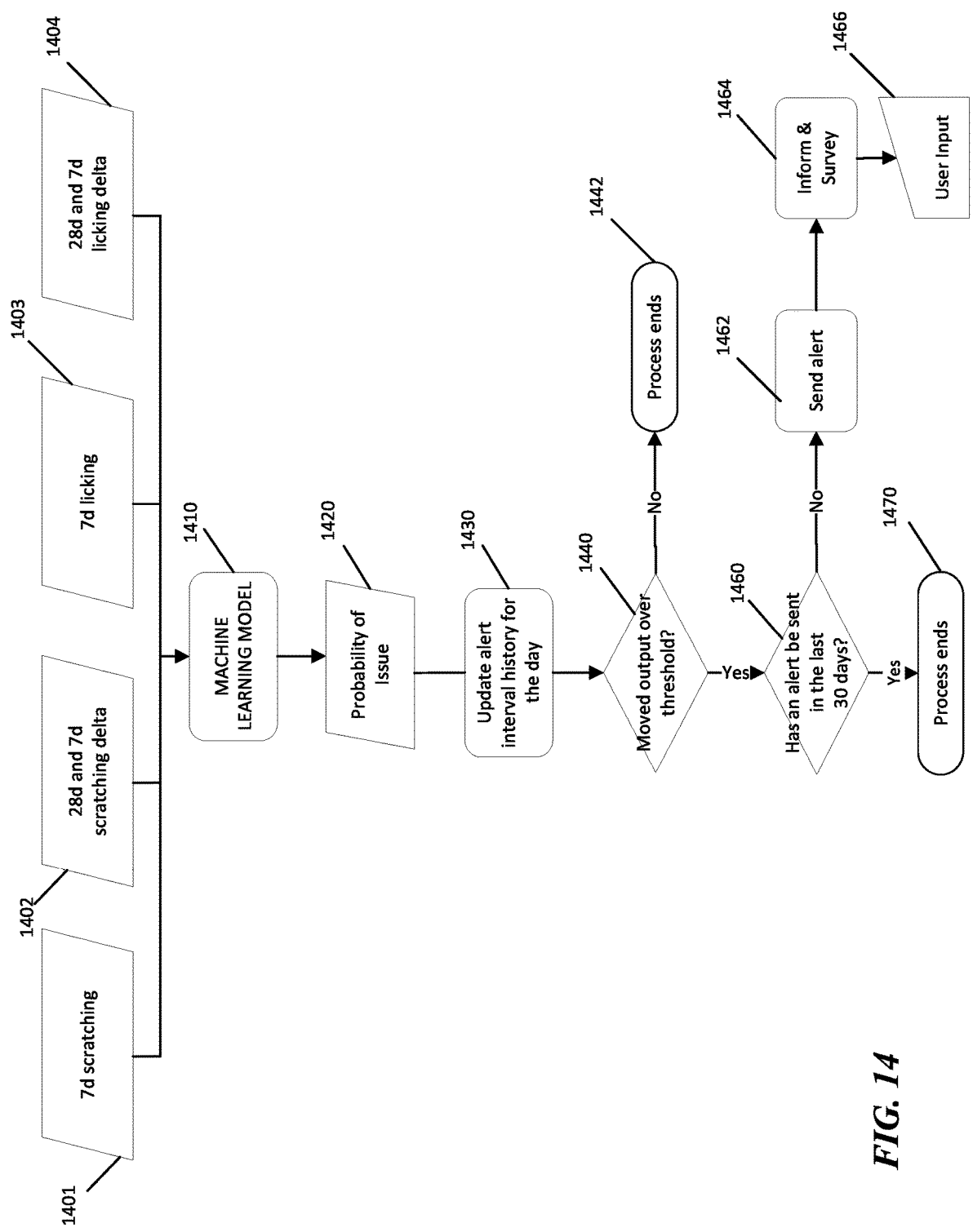
FIG. 14 illustrates a flow diagram of a method and/or process for performing a wellness assessment of a pet according to certain non-limiting embodiments.

FIG. 14 illustrates a flow diagram of a method and/or process for performing a wellness assessment of a pet according to certain non-limiting embodiments. In particular, the method and/or process shown in FIG. 14 can be incorporated into and/or used along with the method and/or process shown in FIG. 4. As discussed above, a model can be trained to detect, determine, and/or predict a health indicator and/or a wellness assessment of a pet. The model, for example, can be trained using at least one of: one or more medical records, one or more behavior aggregations, and/or any combination thereof. Medical records can be used to create labels for the model training process. For example, one or more label(s) can indicate whether or not a pet suffers from a dermatological issue, such as pruritus. Behavior aggregations, on the other hand, can be candidate features for the model. During training, the inputted data can be analyzed to determine features that are helpful in identifying one or more dermatological issue(s). The determined features can be correlated to the one or more dermatological issue. For example, an average level of scratching over a 7-day period can be identified as a helpful feature for identifying a dermatological issue. In certain non-limiting embodiments, to assess a dermatological ailment, a machine learning classifier can be trained on medical records and behavior data from both a treatment group diagnosed with a dermatological condition and a control group without a dermatological condition.

Features, for example, can be a 7-day scratching moving average 1401, a 28-day and 7-day scratching moving average delta 1402 (i.e., a difference in pet movement caused by scratching between a 7-day monitoring period and a 28 day period), a 7-day self-licking moving average 1403, and a 28-day and 7-day self-licking moving average delta 1404 (i.e., a difference in pet movement caused by self-licking between a 7-day monitoring period and a 28-day period). Such features can then be used by the machine learning model 1410 for production. In certain non-limiting embodiments, a structured query language (SQL) query can be used to calculate features 1401-1404 using a standardization scaling step and/or a logistic regression step. The calculation can produce a value between 0 and 1, with the threshold being set at 0.630171.

The machine learning model 1410 can output the probability of a dermatological issue 1420. Based on the probability, one or more of an alert(s), an alarm(s), a notification interval history (and/or notification interval histories), and/or any combination thereof 1430 can be updated. A determination 1440 can then be made whether the probability of a dermatological issue 1420 falls below the threshold, above the threshold, or equal to the threshold. For example, the threshold can be any value between 0 and 1, such as 0.63017. The threshold can be determined to optimize or maximize a balance between false positivity rates and true positivity rates. If the probability falls below a threshold, this means that the probability of a dermatological issue it too low and the process ends 1442.

On the other hand, if the probability falls above a threshold, for example a threshold of 0.63017, a determination 1460 can be made whether the alarm, alert, or notification has been previously sent in the last 30 days. If yes, then the process ends without an additional alarm, alert, or notification sent to the pet owner 1470. If no previous alarm, alert, or notification has been previously sent in the last 30 days, the alarm, alert, or notification can be sent, transmitted, or displayed 1462. The alarm, alert, or notification 1462 can invite the pet owner, or third-party receiving the alarm, alert, or notification, to learn more about the dermatological issue by choosing a link or button on the user interface of the mobile device 1464. If the pet owner or third-party clicks through to learn more about the dermatological alert, the pet owner or third-party can land on an informative page that shows the alert, and/or invites the pet owner or third-party to work through a discovery process to help learn what might be impacting the issue.

In some non-limiting embodiments, the alert(s), alarm(s), and/or notification(s) for a dermatological ailment can be based on a plurality of factors. For example, the scratching and licking levels of a pet can both be considered. Other factors, such as lack of sleep can be considered at one point in time and/or can be added at for consideration at a later time and/or over a particular interval of time. A pet's history and a given breed's sensitivity to a dermatological ailment can also be considered. In other non-limiting embodiments, the sensitivity and/or specificity of the alert(s), alarm(s), and/or notification(s) can be tunable or customized. For instance, the pet's and breed's historical record of incident frequency, along with the historical record of algorithm outputs, can be combined to calculate a threshold parameter that optimizes for, e.g., a desired sensitivity/specificity tradeoff, or for a maximum allowable false positive rate. This customization can help to throttle and/or otherwise avoid repeated and/or unnecessary alert(s), alarm(s) and/or notification(s) for one or more dermatological condition(s), such as one or more chronic dermatological condition(s).

In certain non-limiting embodiments, a pet owner and/or third-party can be asked to fill out a survey or questionnaire 1464. In response, the pet owner or third-party can input information. For example, FIGS. 15 and 16 illustrate an example of a user interface 1510, 1610 according to certain non-limiting embodiments. The user interface 1510 can be used to display a survey or questionnaire 1520 to the pet owner. The survey or questionnaire 1520, as shown in FIG. 15, can include one or more discover variables can be illustrated or displayed on the user interface 1510. The discover variables can be initially defined by a veterinarian as features that can have potential impact on the health indicator or wellness assessment of a pet. For example, the one or more discover variables for a dermatological issue can include a new food, a new treat, a new dog bed, and/or a new supplement being used by the pet. FIG. 15 illustrates a survey or questionnaire 1520 including the one or more discovery variables, while FIG. 16 illustrates additional information requested 1620 from the pet owner based on the response to the survey or questionnaire 1520 in FIG. 15. For example, when a pet owner indicates that a pet is being fed a new food product, the pet owner can be asked to provide additional information related to the new food product, such as "when did you change foods?" "what did you change to," and "why did you change?"

Figure 19:
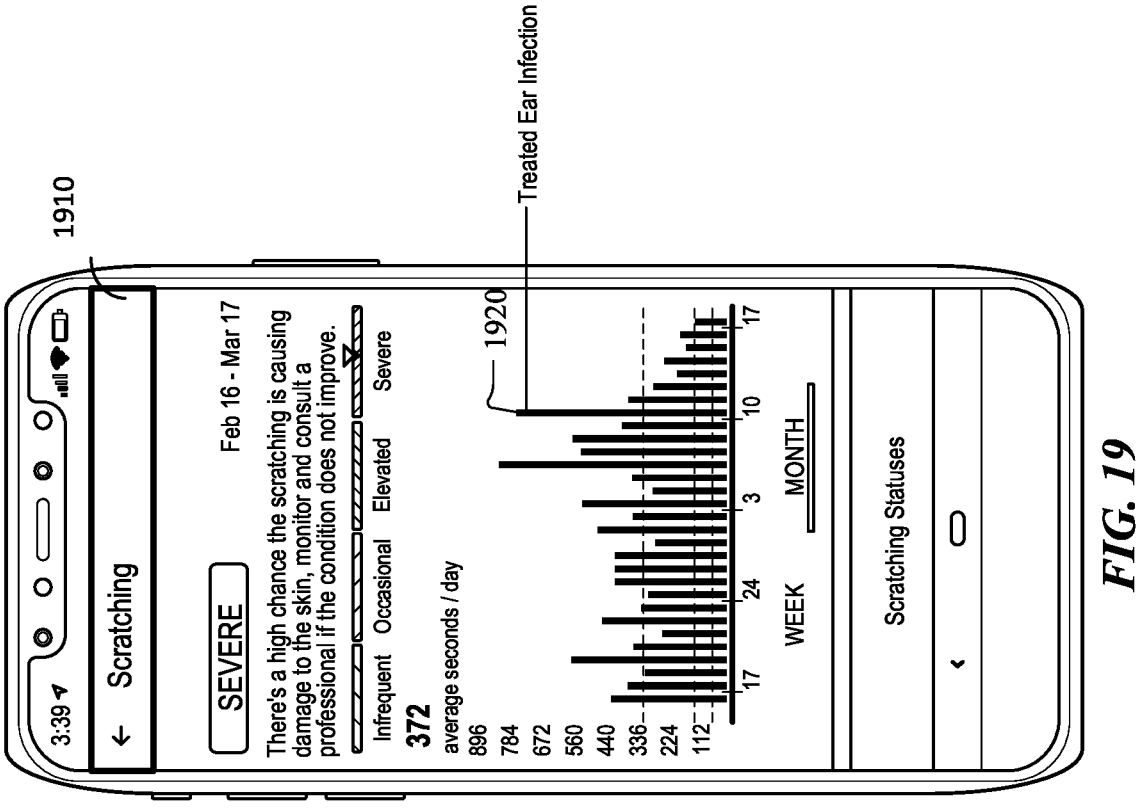
FIGS. 18 and 19 illustrate an example of a user interface providing a causal explanation according to certain non-limiting embodiments.
Figure 18:
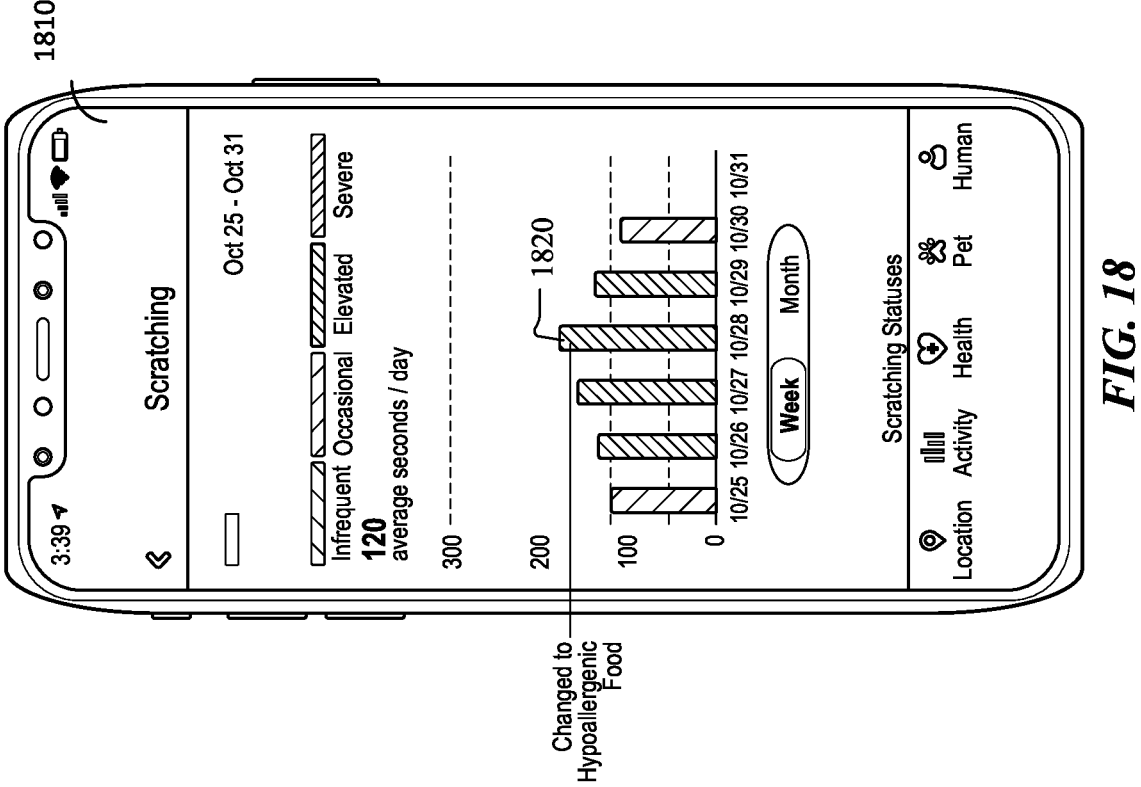

FIG. 17 illustrates an example of a user interface 1710 according to certain non-limiting embodiments. In particular, FIG. 17 can illustrate an alert, alarm, or notification being displayed on a user interface 1710 of a mobile device. The alert, alarm, or notification, for example, can inform the pet owner that the monitored pet is experiencing increased scratching 1720, which can indicate a potential dermatological issue. The survey or questionnaire 1520 shown in FIG. 15 can then be presented to the pet owner. After the pet owner has provided responses to the requested discovery variables, certain non-limiting embodiments can provide a causal explanation 1730 and/or estimated timeline 1740 for the dermatological issue, or any other wellness issue. The server 106 can then send, to the user device (e.g., mobile device 104), instructions for presenting the causal explanation and/or estimated timeline. For example, a new food was consumed by the pet a day before the amount of scratching increased. In some non-limiting embodiments, to determine the causal explanation and/or estimated timeline, we can firstly create visibility of the possible causal relationship to the pet owner and increased accuracy of the history of the pet when seen by the veterinarian. The better history we have on larger numbers of pets, the better abilities we have to make predictions from all of our data inputs. For example, a medication does not work as well in a certain population of pets. We can compare this segment to other data sources such as genetic data to create possible pharmacogenomic discoveries. This also would allow further evaluation of epigenetic factors. The mobile application can then prompt the pet owner to contact a veterinarian. In some other non-limiting embodiments, a button or prompt can be provided to allow a pet owner to call a veterinarian directly from the mobile application. FIGS. 18 and 19 illustrate an example of a user interface 1810, 1910 providing a causal explanation according to certain non-limiting embodiments. FIG. 18 shows the elevated scratching 1820 on October 28 may be due to a change to hypoallergenic food. FIG. 19 shows the severe scratching 1920 on March 11 may be due to a treatment of ear infection.

Beyond providing a wellness assessment and determining the potential cause of the identified pet issue, certain non-limiting embodiments can allow for the assessment of the effectiveness of one or more pet products on the wellness of a pet. The pet products, for example, can include a medication, a pharmaceutical drug, a pet food, or a prescribed treatment by a veterinarian. For example, the pet products can be those products used to treat a dermatological ailment or issue. The server 106 can transmit the determined effectiveness of the pet product to a veterinarian or a manufacturer of the pet product. In some non-limiting embodiments, tracking device 102 and/or server 106 using the predictive model 440 described in FIGS. 4 and 14 can be used to continuously or periodically track a health indicator after a pet product is used to treat a dermatological ailment or issue. For example, the categories of scratching can be tracked for between 0 to 90 days after use of the pet product. In other examples the categories of scratching can be detected for 1 week, 4 weeks, 8 weeks, 10 weeks, 1 year, 2 years, or any other range of time. The post-treatment scratching categories can then be reported to a veterinarian prescribing the treatment. In other non-limiting embodiments, the post-treatment scratching categories can then be reported to a manufacturer of the pet product. The report, for example, can include not only the post-treatment scratching categories of the pet but also the pre-treatment scratching categories of the pet.

The above non-limiting embodiments can help assess the effectiveness of a pet product on the wellness of a pet. While the above examples are generally directed to a single pet, in certain non-limiting embodiments information from a plurality of pets can be aggregated. Such data aggregation can allow for comparison of a plurality of pet products and their respective impact on pet wellness. For example, if 9 different pet products are generally prescribed to treat a pruritus, a comparison of the effectiveness of the 9 different pet products can be conducted based on aggregated measurements of individual pets that are monitored using tracking device 102 and/or server 106.

In one non-limiting embodiment, a comparison of medications to treat pruritus in dogs can be performed. The medications, for example, can be a first medication, a second medication, or any one of eight other medications referred to as other medications. 131 dogs were treated using the first medication, 164 dogs were treated using the second medication, 70 dogs were treated using other medications, and 82 dogs were not treated with any medications. All dogs averaged a decrease in scratching from the week prior to the veterinarian visit to the week after the visit. Dogs that received medication, however, averaged a larger reduction. Dogs that did not receive treatment showed only a slight change due to the visit and averaged a higher amount of scratching during the first week after the visit than the dogs that received the medication. Dogs treated with the first medication returned to pre-visit category of scratching approximately 5 weeks after the visit, and dogs treated with the second medication returned to pre-visit category of scratching approximately 6 to 8 weeks after the visit.

Figure 20:
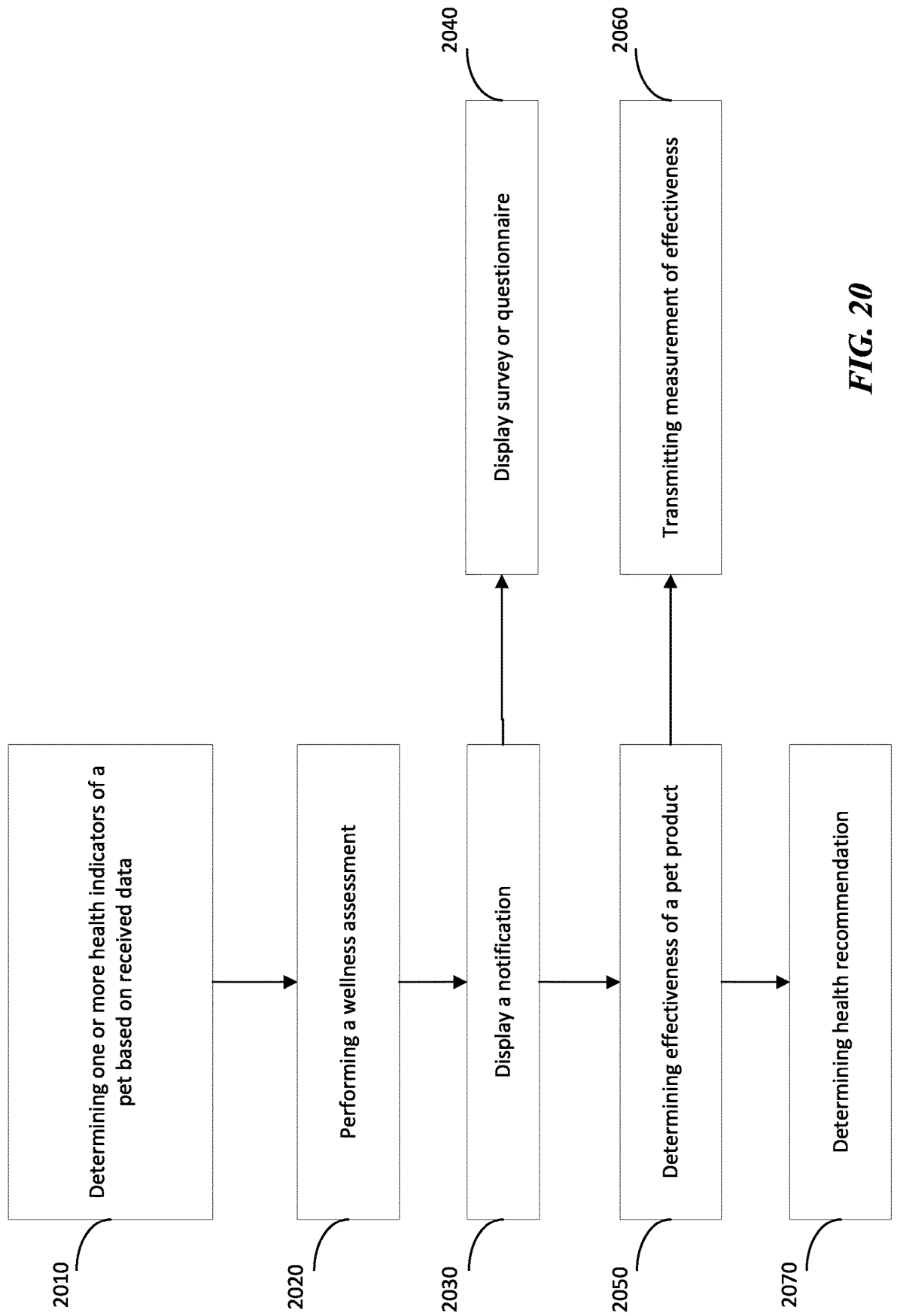
FIG. 20 illustrates a flow diagram of a method or process according to certain non-limiting embodiments.

FIG. 20 illustrates a flow diagram of a method or process according to certain non-limiting embodiments. In step 2010, one or more health indicators of a pet can be determined based on collected, received and/or analyzed data. The data can be collected, received and/or analyzed from (or by) one or more sensors of a wearable device on a pet. The one or more sensors can include at least one of: one or more actuator(s), one ore more gyroscope(s), one or more magnetometer(s), one or more microphone(s), one or more pressure sensor(s), and/or any combination thereof. In other embodiments, the collected, received and/or analyzed data can include one or more health record(s) of a pet, demographic information of the pet, location of the pet, and/or weather information of the location of the pet. In step 2020, a wellness assessment of the pet can be performed based on the one or more health indicators of the pet. In some non-limiting embodiments, a wellness assessment of the pet can be performed based on the one or more health indicators. The wellness assessment, for example, can include evaluation and/or detection of dermatological condition(s), dermatological ailment, issue, or disease(s), such as pruritus, ear/eye infection, arthritis, cardiac episode(s), cardiac condition(s), cardiac disease(s), allergies, dental condition(s), dental disease(s), kidney condition(s), kidney disease(s), cancer, endocrine condition(s), endocrine disease(s), deafness, depression, pancreatic episode(s), pancreatic condition(s), pancreatic disease(s), obesity, metabolic condition(s), metabolic disease(s), and/or any combination thereof. The wellness assessment can also include any other health condition, diagnosis, or physical or mental disease or disorder currently known in veterinary medicine.

In step 2030, an alert(s), alarm(s) and/or notification(s) to a pet owner can be displayed at a mobile device based on the wellness assessment of the pet. In addition, or alternatively, the notification can be transmitted based on the wellness assessment of the pet to the mobile device of the pet owner. In some non-limiting embodiments, a survey or questionnaire corresponding to the wellness assessment of the pet can be displayed at the graphical user interface of the mobile device, as shown in step 2040. In step 2050, effectiveness of a pet product can be determined based on the one or more health indicators. In step 2060, a measurement of the effectiveness of the pet product can be transmitted to a veterinarian or a manufacturer of the pet product. In step 2070, a health recommendation of the pet can be determined based on the wellness assessment.

FIG. 21 illustrates an example method 2100 for pet wellness assessment. The method may begin at step 2110, where the server 106 may access sensor data captured by one or more sensors, wherein the sensor data is associated with a first pet. At step 2120, the server 106 may detect, based on the sensor data, one or more activities of the first pet within a specified time period. At step 2130, the server 106 may determine, based on one or more of the activities, one or more health indicators of the first pet, wherein the one or more health indicators are based on one or more metrics associated with the one or more of the activities. At step 2140, the server 106 may generate a wellness assessment of the first pet based on the one or more health indicators, wherein the wellness assessment comprises one or more of a wellness score or an alert of a possible medical condition from a plurality of medical conditions. At step 2150, the server 106 may send, to a user device, instructions for presenting the wellness assessment of the first pet to a user. Particular embodiments may repeat one or more steps of the method of FIG. 21, where appropriate. Although this disclosure describes and illustrates particular steps of the method of FIG. 21 as occurring in a particular order, this disclosure contemplates any suitable steps of the method of FIG. 21 occurring in any suitable order. Moreover, although this disclosure describes and illustrates an example method for pet wellness assessment including the particular steps of the method of FIG. 21, this disclosure contemplates any suitable method for pet wellness assessment including any suitable steps, which may include all, some, or none of the steps of the method of FIG. 21, where appropriate. Furthermore, although this disclosure describes and illustrates particular components, devices, or systems carrying out particular steps of the method of FIG. 21, this disclosure contemplates any suitable combination of any suitable components, devices, or systems carrying out any suitable steps of the method of FIG. 21.

While some of the data described above reflects pet activity data, in certain non-limiting embodiments other data, which does not reflect pet activity, can be collected, processed and/or analyzed using the activity recognition time series classification algorithm to infer a desired output time series. For example, other data can include, but is not limited to, financial data, cyber security data, data from electronic health record(s), acoustic data, image or video data, human activity data, and/or any other data known in the art. In such embodiments, the input(s) of the time series can exist in a wide range of different domains, including finance, cyber security, electronic health record analysis, acoustic scene classification, and human activity recognition. The data, for example, can be time series data. In addition, or as an alternative, the data can be first-party data, such as data obtained from a wearable device, or third-party data. Third-party data can include data that is not directly collected by a given company or entity, but rather data that is purchased from other collecting entities or companies. For example, the third-party data can be accessed or purchased using a data-management platform. First-party data, on the other hand, can include data that is directly owner and/or collected by a given company. For example, first-party data can be collected from consumers using products or services offered by the given company, such as a wearable device.

In certain non-limiting embodiments, a system, method, and/or apparatus can be used to assess pet wellness. As described above, data related to the pet can be collected, received and/or analyzed. The data can be collected by and/or received from at least one of the following data sources: one or more wearable pet tracking and/or monitoring device(s), genetic testing procedure(s), pet health record(s), pet insurance record(s), input from the pet owner(s), and/or any combination thereof. One or more of the above data sources can collected using separate sources, such as separate pet health record(s) and/or separate pet health tracking device(s). After data is collected and/or received, it can be aggregated into one or more databases. The process or method can be performed by any device, hardware, software, algorithm, cloud-based server, and/or any combination thereof, for example, as described herein.

Based on the collected and/or received data, one or more health indicators of a pet can be determined. For example, the health indicator(s) can include a metric for one or more of: licking, scratching, itching, walking, sleeping, and/or any combination thereof by the pet. For example, a metric can be the number of minutes per day a pet spends sleeping, and/or the number or minutes per day a pet spends walking, running, and/or otherwise being active. Any other metric that can indicate the health of a pet can be determined. Based on the wellness assessment, a recommendation can be determined and transmitted to one or more of a pet owner, a veterinarian, a researcher, a manufacturer, and/or any combination thereof. The recommendation, for example, can include one or more health recommendations for preventing the pet from developing one or more of a disease, a condition, an illness and/or any combination thereof. The recommendation, for example, can include one or more of: a food product, a pet service, a supplement, an ointment, a drug to improve the wellness or health of the pet, a pet product, and/or any combination thereof. In other words, the recommendation can be a nutritional recommendation. In some embodiments, a nutritional recommendation can include an instruction to feed a pet one or more of: a chewable, a supplement, a food and/or any combination thereof. In some embodiments, the recommendation can be a medical recommendation. For example, a medical recommendation can include an instruction to apply an ointment to a pet, to administer one or more drugs to a pet and/or to provide one or more drugs for or to a pet.

The embodiments disclosed herein can benefit the pet care industry as follows. Certain embodiments can create the foundations for democratizing care through an objective understanding of what is happening in a pet's life. Certain embodiments can also create context for what an alert means and what is recommended next steps. In addition, certain embodiments can complement veterinary professionals by extending into the known care desert that lies between the pet home and the clinic. In particular, the embodiments disclosed herein can enable early detection for pet issues, thereby early intervention. Early intervention is a win for the pet, the pet owner, and the veterinarian dealing with a frustrating recurring condition. For example, for pruritic skin disease, the embodiments disclosed herein can help reduce the cost of treatment and improve antibiotic sparing. Early pruritus detection and intervention in chronic atopy cases can help prevent one of the more common reasons for a pet to develop resistant infections.

In certain non-limiting embodiments, a health wellness assessment and/or recommendations can be based on data that includes information pertaining to a plurality of pets. In other words, the health indicators of a given pet can be compared to those of a plurality of other pets. Based on this comparison, a wellness assessment of the pet can be performed, and appropriate recommendations can be provided. In some non-limiting embodiments, the wellness assessment and recommendations can be customized based on the health indicators of a single pet. For example, instead of relying on data collected from a plurality of other pets, the determination can be based on algorithms or modules that are tuned or trained based wholly or in part on data or information related to the behavior of a single pet. Recommendations for pet products or services can then be customized to the behaviors or specific health indicators of a single pet.

As discussed above, the health indicator(s), for example, can include a metric for one or more of: licking, scratching, itching, walking, sleeping and/or any combination thereof by the pet. These health indicator(s) can be determined based on data, information, or metrics collected and/or received from and/or analyzed by a wearable device having one or more sensor(s) and/or one or more accelerometer(s). The collected data from the wearable device can then be processed and/or analyzed by an activity recognition algorithm or model, also referred to as an activity recognition module or algorithm, to determine or identify one or more health indicator(s). The activity recognition algorithm or model can include two or more of the layer modules described above. After the health indicator is identified, in certain non-limiting embodiments the pet owner can be asked to verify the correctness of the health indicator. For example, the pet owner can receive a short message service, an alert or notification, such as a push alert, an electronic mail message on a mobile device, or any other type of message or notification. The message or notification can request the pet owner to confirm the health indicator identified by the activity recognition algorithm or model. In some non-limiting embodiments, the message or notification can indicate a time during which the data, information, or metrics were collected. If the pet owner cannot confirm the health indicator, the pet owner can be asked to input the activity of the pet at the indicated time.

In certain non-limiting embodiments, the pet owner can deny the occurrence of the one or more health indicator(s) during the indicated time and does not provide information related to the pet's activity during the indicated time. For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module can be stored on a computer readable medium for execution by a processor. Modules can be integral to one or more servers, or be loaded and executed by one or more servers. One or more modules can be grouped into an engine or an application.

For the purposes of this disclosure the term "user", "subscriber" "consumer" or "customer" should be understood to refer to a user of an application or applications as described herein and/or a consumer of data supplied by a data provider. By way of example, and not limitation, the term "user" or "subscriber" can refer to a person who receives data provided by the data or service provider over the Internet in a browser session, or can refer to an automated software application which receives the data and stores or processes the data.

Those skilled in the art will recognize that the methods and systems of the present disclosure can be implemented in many manners and as such are not to be limited by the foregoing exemplary embodiments and examples. In other words, functional elements being performed by single or multiple components, in various combinations of hardware and software or firmware, and individual functions, can be distributed among software applications at either the client level or server level or both. In this regard, any number of the features of the different embodiments described herein can be combined into single or multiple embodiments, and alternate embodiments having fewer than, or more than, all of the features described herein are possible.

Functionality can also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that can be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications can be made to the elements and operations described above to obtain a result that remains within the scope of the systems and processes described in this disclosure.

While the disclosed subject matter is described herein in terms of certain preferred embodiments, those skilled in the art will recognize that various modifications and improvements can be made to the disclosed subject matter without departing from the scope thereof. Moreover, although individual features of one non-limiting embodiment of the disclosed subject matter can be discussed herein or shown in the drawings of the one non-limiting embodiment and not in other embodiments, it should be apparent that individual features of one non-limiting embodiment can be combined with one or more features of another embodiment or features from a plurality of embodiments.

What is claimed is:

1. A method for generating a wellness assessment of a pet based on sensor data comprising, by one or more computing systems:

receiving, by one or more processors, sensor data associated with a pet from one or more sensors, wherein the one or more sensors are associated with a wearable device worn by or attached to the pet, the sensor data including:

a time value corresponding to when the pet performed an activity, and an intensity point corresponding to when the pet performed the activity;

detecting, by the one or more processors, an orientation of the wearable device, wherein the orientation is calculated based on rotation data of the wearable device;

transforming, by the one or more processors, the sensor data into a consistent coordinate system based on the orientation of the wearable device, wherein transforming the sensor data includes modifying the sensor data based on the rotation data;

executing, by the one or more processors, an algorithm to generate a baseline value for the activity based on aggregated activity data of a plurality of similar pets, wherein the plurality of similar pets comprises pet data of a same pet breed, a same pet age, or a same pet weight as the pet;

predicting, by the one or more processors, one or more health indicators corresponding to the pet based on the transformed sensor data, wherein the one or more health indicators include one or more metrics associated with the activity;

executing, by the one or more processors, the algorithm on the one or more health indicators to generate a wellness assessment of the pet, wherein the wellness assessment includes an energy expenditure wellness value of the pet determined based on the time value the pet performed the activity at the intensity point compared to a goal intensity point, wherein the goal intensity point is calculated based on the baseline value for the activity and the received intensity point for the pet;

determining, by the one or more processors, a pet recommendation by inputting the wellness assessment of the pet into a prediction module trained on previous pet data corresponding to the pet, wherein the pet recommendation includes a medical recommendation or a product recommendation; and transmitting, by the one or more processors, an alert that includes the pet recommendation to a user interface of a user device.

2. The method of claim 1, wherein the one or more sensors further comprise one or more of an actuator, a gyroscope, a magnetometer, a microphone, or a pressure sensor.

3. The method of claim 1, wherein detecting the orientation of the wearable device further comprises:

training, by the one or more processors, a convolutional neural network with training data to determine an orientation of the wearable device on a pet collar, wherein the training data is associated with a known orientation of the wearable device.

4. The method of claim 1, wherein generating the wellness assessment of the pet further comprises:

training, by the one or more processors, the prediction module based on one or more of health status data, demographic information, genetic data, location, weather information of the location, or environment data of the location.

5. The method of claim 1, further comprising:

comparing, by the one or more processors, at least one of the predicted health indicators to at least one stored corresponding health indicator; and detecting, by the one or more processors, a threshold difference between the at least one predicted health indicator and the at least one stored corresponding health indicator;

wherein the wellness assessment further comprises the detected threshold difference between the at least one predicted health indicator and the at least one stored corresponding health indicator.

6. The method of claim 1, wherein the method further comprises:

rescaling, by the one or more processors, one or more of the metrics into a predetermined range; and generating, by the one or more processors, the one or more energy expenditure wellness values based on the one or more rescaled metrics.

7. The method of claim 1, wherein the one or more health indicators are associated with one or more weights, respectively, wherein the method further comprises:

generating, by the one or more processors, the one or more energy expenditure wellness values based on the one or more weights.

8. The method of claim 1, wherein the activity comprises one or more of:

a posture comprising one or more of a lying down posture, a sitting posture, a standing posture, a walking posture, or a vigorous posture; or a behavior comprising one or more of a drinking behavior, an eating behavior, a licking an object behavior, a self-licking behavior, a petting behavior, a rubbing behavior, a scratching behavior, a shaking behavior, or a sniffing behavior.

9. The method of claim 1, wherein the medical recommendation corresponds to a medical condition including at least one of: a dermatological condition, an ear infection, arthritis, a cardiac episode, a gastrointestinal condition, malaise, a tooth fracture, a cruciate ligament tear, or a pancreatic episode.

10. The method of claim 1, wherein the wellness assessment comprises one or more alerts of a possible medical condition, wherein the method further comprises:

generating an estimated timeline for the possible medical condition; and presenting, via the user interface on the user device, the estimated timeline.

11. A non-transitory computer-readable medium storing instructions that, when executed by one or more processors, cause the one or more processors to:

receive sensor data associated with a pet captured by one or more sensors, wherein the one or more sensors are associated with a wearable device worn by or attached to the pet, the sensor data including:

a time value corresponding to when the pet performed an activity, and an intensity point corresponding to when the pet performed the activity-detect an orientation of the wearable device, wherein the orientation is calculated based on rotation data of the wearable device;

transform the sensor data into a consistent coordinate system based on the orientation of the wearable device, wherein transforming the sensor data includes modifying the sensor data based on the rotation data;

execute an algorithm to generate a baseline value for the activity based on aggregated activity data of a plurality of similar pets, wherein the plurality of similar pets comprises pet data of a same pet breed, a same pet age, or a same pet weight as the pet;

predict one or more health indicators corresponding to the pet based on the transformed sensor data, wherein the one or more health indicators include one or more metrics associated with the activity;

execute the algorithm on the one or more health indicators to generate a wellness assessment of the pet, wherein the wellness assessment includes an energy expenditure wellness value of the pet determined based on the time value the pet performed the activity at the intensity point compared to a goal intensity point, wherein the goal intensity point is calculated based on the baseline value for the activity and the received intensity point for the pet;

determine a pet recommendation by inputting the wellness assessment of the pet into a prediction module trained on previous pet data corresponding to the pet, wherein the pet recommendation includes a medical recommendation or a product recommendation; and transmit an alert that includes the pet recommendation to a user interface of a user device.

12. A system comprising:

one or more processors; and a memory storing instructions that, when executed by the one or more processors, cause the processors to:

receive sensor data associated with a pet captured by one or more sensors, wherein the one or more sensors are associated with a wearable device worn by or attached to the pet, the sensor data including:

a time value corresponding to when the pet performed an activity, and an intensity point corresponding to when the pet performed the activity-detect an orientation of the wearable device, wherein the orientation is calculated based on rotation data of the wearable device;

transform the sensor data into a consistent coordinate system based on the orientation of the wearable device, wherein transforming the sensor data includes modifying the sensor data based on the rotation data;

execute an algorithm to generate a baseline value for the activity based on aggregated activity data of a plurality of similar pets, wherein the plurality of similar pets comprises pet data of a same pet breed, a same pet age, or a same pet weight as the pet;

predict one or more health indicators corresponding to the pet based on the transformed sensor data, wherein the one or more health indicators include one or more metrics associated with the activity;

execute the algorithm on the one or more health indicators to generate a wellness assessment of the pet, wherein the wellness assessment includes an energy expenditure wellness value of the pet determined based on the time value the pet performed the activity at the intensity point compared to a goal intensity point, wherein the goal intensity point is calculated based on the baseline value for the activity and the received intensity point for the pet;

determine a pet recommendation by inputting the wellness assessment of the pet into a prediction module trained on previous pet data corresponding to the pet, wherein the pet recommendation includes a medical recommendation or a product recommendation; and transmit an alert that includes the pet recommendation to a user interface of a user device.

13. The system of claim 12, wherein the one or more sensors further comprise one or more of an actuator, a gyroscope, a magnetometer, a microphone, or a pressure sensor.

14. The system of claim 12, wherein the instructions, when executed, further cause the one or more processors to:

train a convolutional neural network with training data to determine an orientation of the wearable device on the pet collar, wherein the training data is associated with a known orientation of the wearable device.

15. The system of claim 12, wherein the instructions, when executed, further cause the one or more processors to:

train the prediction module based on one or more of health status data, demographic information data, genetic data, location data, weather information data of the location, or environment data of the location.

16. The system of claim 12, wherein the instructions, when executed, further cause the one or more processors to:

compare at least one of the predicted health indicators to at least one stored corresponding health indicator; and detect a threshold difference between the at least one predicted health indicator and the at least one stored corresponding health indicator;

wherein the wellness assessment further comprises the detected threshold difference between the at least one predicted health indicator and the at least one stored corresponding health indicator.

17. The system of claim 12, wherein the instructions, when executed, further cause the one or more processors to:
rescale one or more of the metrics into a predetermined range; and
generate the one or more energy expenditure wellness values based on the one or more rescaled metrics.

18. The system of claim 12, wherein the one or more health indicators are associated with one or more weights, respectively, wherein the instructions, when executed, further cause the one or more processors to:
generate the one or more energy expenditure wellness values based on the one or more weights.

19. The system of claim 12, wherein the activity comprises one or more of:
a posture comprising one or more of a lying down posture, a sitting posture, a standing posture, a walking posture, or a vigorous posture; or
a behavior comprising one or more of a drinking behavior, an eating behavior, a licking an object behavior, a self-licking behavior, a petting behavior, a rubbing behavior, a scratching behavior, a shaking behavior, or a sniffing behavior.

20. The system of claim 12, wherein the medical recommendation corresponds to a medical condition including at least one of: a dermatological condition, an ear infection, arthritis, a cardiac episode, a gastrointestinal condition, malaise, a tooth fracture, a cruciate ligament tear, or a pancreatic episode.

\* \* \* \* \*